United States Patent
Tricoli et al.

(10) Patent No.: US 6,361,948 B1
(45) Date of Patent: Mar. 26, 2002

(54) PROGNOSTIC COMPOSITIONS FOR PROSTATE CANCER AND METHODS OF USE THEREOF

(76) Inventors: James V. Tricoli, 106 Clover Leaf La., North Wales, PA (US) 19454; Rachel Rondinelli, 418 Candlewood Way, Harleysville, PA (US) 19438

( * ) Notice: Subject to any disclaimer, the term of this patent is extended or adjusted under 35 U.S.C. 154(b) by 0 days.

(21) Appl. No.: 09/485,549

(22) PCT Filed: Aug. 13, 1998

(86) PCT No.: PCT/US98/16768

§ 371 Date: Nov. 9, 2000

§ 102(e) Date: Nov. 9, 2000

(87) PCT Pub. No.: WO99/09215

PCT Pub. Date: Feb. 25, 1999

Related U.S. Application Data

(60) Provisional application No. 60/055,285, filed on Aug. 13, 1997.

(51) Int. Cl.⁷ .......................... C12Q 1/68; C12P 19/34; C07H 21/04; C07K 1/00
(52) U.S. Cl. ........................... 435/6; 435/7.1; 536/23.5; 530/350; 530/387.1
(58) Field of Search ........................... 436/6, 91.2, 7.1, 436/252.3, 320.1; 530/350, 387.1; 536/23.5, 24.31, 24.33

(56) References Cited

PUBLICATIONS

EST Accession #W73033, Oct. 16, 1996.*
Rondinelli et al., Proc. Am. Assoc. Cancer es. Ann. Meeting 38(0), 420–421 (1997).*
Rondinelli et al., Clin. Cancer Res. 5(6), 1595–1602 (1999).*
The Natural History of Prostatic Cancer—Willet F. Whitmore, Jr., M.D., Cancer, Nov. 1973, pp. 1104–1112.
Cancer Statistics, 1996 —Sheryl L. Parker, et al.; CA Cancer J Clin 1996:65:5–27; vol. 46, No. 1, Jan./Feb. 1996.
Pathologic and Clinical Findings to Predict Tumor Extent of Nonpalpable (Stage T1c) Prostate Cancer—Jonathan I. Epstein et al.; Jama, Feb. 2, 1994–vol. 271, No. 5.
Experience With Gleason's Histopathologic Grading In Prostatic Cancer—Stephen A. Kramer et al.; The Journal of Urology, vol. 124, Aug., pp. 223–225.
Identification of High Mobility Group Protein I(Y) as Potential Progression Marker for Prostate Cancer by Differential Hybridization Analysis—Marion J. G. Bussemakers et al.; Cancer Research 51, 606–611, Jan. 15, 1991.
Cytidine methylation of regulatory sequences near the π–class glutathione S–transferase gene accompanies human prostatic carcinogenesis—Wen–Hsiang Lee et al.; Proc. Natl. Acad. Sci. USA, vol. 91, pp. 11733–11737, Nov. 1994, Medical Sciences.

Markers of the Metastatic Phenotype in Prostate Cancer—C. S. Foster et al.; Human Pathology, vol. 23 No. 4 (Apr. 1992), pp. 381–394.
Decreased E–Cadherin Expression Is Associated with Poor Prognosis in Patients with Prostate Cancer—Rainy Umbas et al.; Cancer Research 54, 3929–3933, Jul. 15, 1994.
Decreased Expression of E–Cadherin in the Progression of Rat Prostatic Cancer—Marion J. G. Bussemakers et al.; Cancer Research 52, 2916–2922, May 15, 1992.
Differential Expression Of Vimentin In Rate Prostatic Tumors; Marion J.G. Bussemakers et al.; Feb. 14, 1992; Biochemical and Biophysical Research Communications; pp. 1254–1259.
Reduction of E–Cadherin Levels and Deletion of the α–Catenin Gene in Human Prostate Cancer Cells—Ronald A. Morton et al.; Cancer Research 53, 3585–3590, Aug. 1, 1993.
KAI1, a Metastasis Suppressor Gene for Prostate Cancer on Human Chromosome 11p11.2—Jin–Tang Dong et al.; Science, vol. 268, May 12, 1995, pp. 884–886.
A rapid and simple PCR–based method for isolation of cDNAs from differentially expressed genes—Boris P. Sokolov et al.;, Nucelic Acids Research, 1994, vol. 22, No. 19, pp. 4009–4015.
Expression of the Cellular Adhesion Molecule E–Cadherin Is Reduced or Absent in High–Grade Prostate Cancer—Rainy Umbas et al.; Cancer Research 52, 5104–5109, Sep. 15, 1992.
Enhanced Levels of Insulin–like Growth Factor Messenger RNA in Human Colon Carcinomas and Liposarcomas—James V. Tricoli et al.; Cancer Research 46, 6169–6173, Dec., 1986.
Alterations of the Retinoblastoma Gene in Human Prostate Adenocarcinoma—James V. Tricoli et al.; Genes, Chromosomes & Cancer 15:108–114 (1996).
Mapping small DNA sequences by fluorescence in situ hybridization directly on banded metaphase chromosomes—Yao–Shan Fan et al.; Proc. Natl. Acad.Sci. USA, vol. 87, pp. 6223–6227, Aug. 1990, Genetics.
Chromosomal localization of a gene, GFI1, encoding a novel zinc finger protein reveals a new syntenic region between man and rodents—D.W. Bell et al.; Cytogenet Cell Genet 70:263–267(1995).

* cited by examiner

Primary Examiner—Kenneth R. Horlick
(74) Attorney, Agent, or Firm—Dean Dorfman Herrell & Skillman

(57) ABSTRACT

This invention provides a novel nucleic acid molecule, CLAR1, isolated from a human adult heart cDNA library. This cDNA is derived from a novel gene that represents a late stage-specific marker for prostate cancer progression. The CLAR1 cDNA, along with its encoded protein and antibodies thereto, provides a biological marker for aggressive prostate cancer.

19 Claims, 8 Drawing Sheets

Relative Increase in Clar1 2.0 kb Transcript vs 2.6 kb Transcript

Predicted Clar1 Protein (33.8 kDa)

```
  1  MSFEGGDGAG  PAMLATGTAR  MASGRPEELW  EAVVGAAAERF  RARTGTELVL
 51  LTAAPPPPPR  PGPCAYAAHG  RGALAEAARR  CLHDIALAHR   AATAARLPAP
101  PPAPQPPSPT  PSPPRPTLAR  EDNEEDEDEP  TETETSGEQL   GISDNGGLFV
151  MDEDATLODL  PPFCESDPES  TDDGSLSEET  PAGPPTCSVP   PASALPTOQY
201  AKSLPVSVPV  WGFKEKRTEA  RSSDGENGPP  SSPDLDRIAA   SMRALVLREA
251  EDTQVFGDLP  RPRLNTSDFQ  KLKRKY
```

\* The 14A1 differential display clone position is indicated by the underline and it extends 269 bp beyond the stop codon.

Fig. 6A

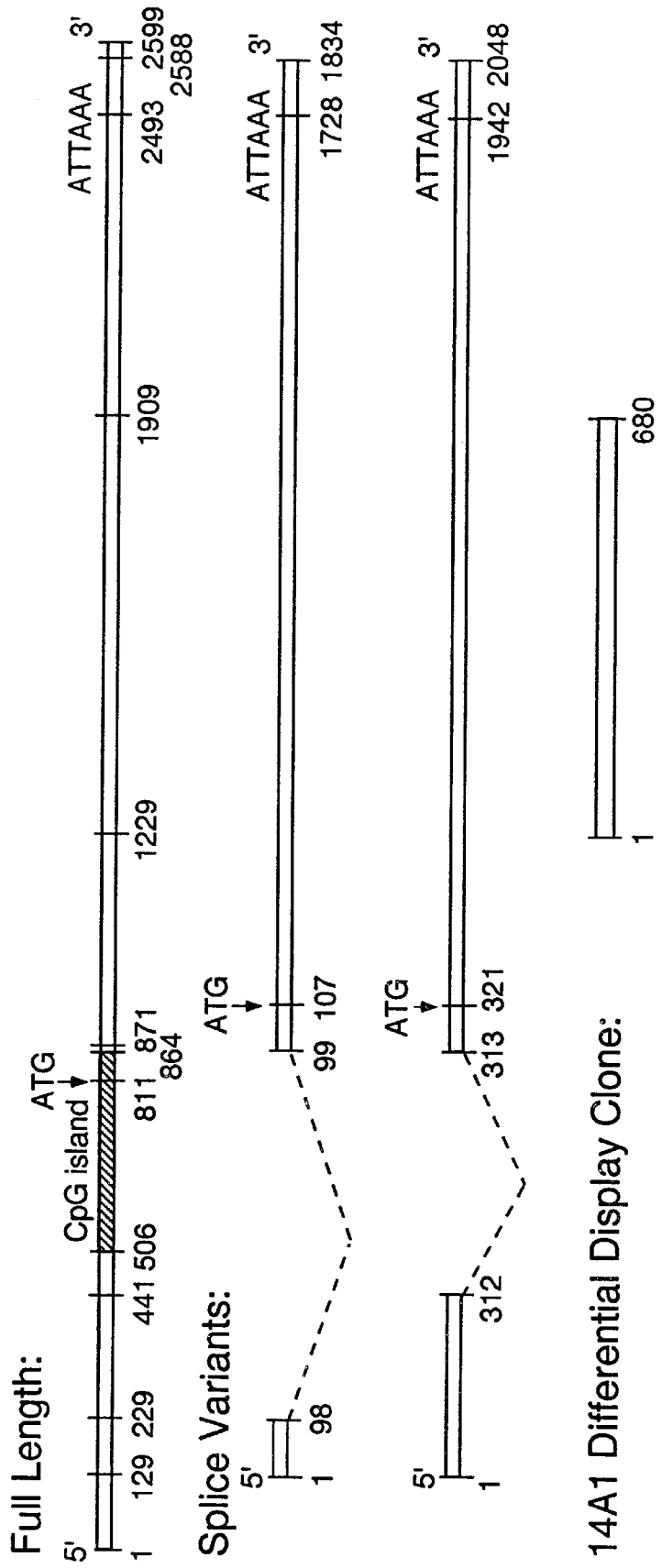

SEQUENCE LISTING

```
<160> NUMBER OF SEQ ID NOS: 10

<210> SEQ ID NO 1
<211> LENGTH: 1835
<212> TYPE: DNA
<213> ORGANISM: Homo sapiens

<400> SEQUENCE: 1
ggcataagcc ggtcagctaa ggccatgtta atacggggct gtcccatctc tctgcggggc      60
gcgacagctg aagagccga acggataata gaagaggagg gcgcggatgg cgtcggggcg     120
ccccgaggag ctgtgggagg ccgtggtggg ggccgctgag cgcttccggg cccggactgg     180
cacggagctg gtgctgctga ccgcggcccc gccgccacca ccccgcccgg gccctgtgc     240 ctatgctgcc catggtcgag gagccctggc ggaggcagcg cgccgttgcc tccacgacat     300
cgcactggcc cacagggctg ccactgctgc tcggcttcct gcgcccccac cagcaccaca     360
gccacccagt cccacaccca gcccaccccg gcctaccctg gcagagagg acaacgagga      420 ggacgaggat gagcccacag agacagagac ctccggggag cagctgggca ttagtgataa     480
tggagggctc tttgtgatgg atgaggacgc caccctccag gaccttcccc ccttctgtga     540
gtcagacccc gagagtacag atgatggcag cctgagcgag gagaccccg ccggcccccc      600 cacctgctca gtgcccccag cctcagccct acccacacag cagtacgcca agtccctgcc     660
tgtgtctgtg cccgtctggg gcttcaagga gaagaggaca gaggcgcggt catcagatgg     720
ggagaatggg ccgccctctt cgcccgacct ggaccgcatc gcggcgagca tgcgcgcgct     780
ggtgctgcga gaggccgagg acacccaggt cttcggggac ctgccacggc cgcggcttaa     840
caccagcgac ttccagaagc tgaagcggaa atattgaagt ccagggaggg agcgccccgg     900
gccgcgtccg ccccgtccca caatacgccc ccgccccact cccggggcct gctaatctga     960
ggccgatccg ggaccggcct ccttgcgtct cccattccca agattgtccc gcctctgcca    1020
atccccgccg tccttccagc ccacgacctg ccgcgccgag gagcggcatc tgtcccgttt    1080
```

```
cccgattggg tctgtcgtct ctctccgcct agcgacagat tccttctatt aagggattgg    1140
ctcgctgagt tctaagctct aaatgggtca actcctttgt tttccgccta gcgacaaggg    1200
atttgctcgc acggcattgg ctccatcccc tagtcgctgg acagctcttt ttttgattgg    1260
ctcaaatcct gtaaagggct tgaccagtct ctacatagtc accgtccgct tttcctgagt    1320
tctccctccc aattggctcc agcttcctgg gggcgtggcc aagccctcct cttcccagaa    1380
ttggcccggg gccttcaatt tacgttttt acactacggg gactggggtt gtctttgccc      1440
acgtcccgac aaattgttcc ctgaccccct cagggatggc cccaaactgt ccctgcctct    1500
ggcaccccct ttcattggtt ccatccatcc ccacaacagc ctgccaatcg aagcccgtcc    1560
ctgcatccag gatggtacca gttcccgccc ctcgccccc acctccacag gtgccttaaa      1620
gggccctcgt ccacccaagg tgggggcag gggccctcac tttccggccc tggtgtgggg     1680
gagagagtga ggggttgggg gatcggcagt tgggaggggc gctctgagat taaagagttt    1740
tacctttggg gtaaaaaaa aaaaaaaaa aaaaaaaaa aaaaaaaaa aaaaaaaaa       1800 aaaaaaaaa aaaaaaaaa aaaaaaaaa aaaaa                                  1835

<210> SEQ ID NO 2
<211> LENGTH: 276
<212> TYPE: PRT
<213> ORGANISM: Homo sapiens

<400> SEQUENCE: 2

Met Ser Phe Glu Gly Gly Asp Gly Ala Gly Pro Ala Met Leu Ala Thr
 1               5                  10                  15

Gly Arg Ala Arg Met Ala Ser Gly Arg Pro Glu Glu Leu Trp Glu Ala
            20                  25                  30

Val Val Gly Ala Ala Glu Arg Phe Arg Ala Arg Thr Gly Thr Glu Leu
        35                  40                  45

Val Leu Leu Thr Ala Ala Pro Pro Pro Pro Arg Pro Gly Pro Cys
    50                  55                  60

Ala Tyr Ala Ala His Gly Arg Gly Ala Leu Ala Glu Ala Ala Arg Arg
65                  70                  75                  80

Cys Leu His Asp Ile Ala Leu Ala His Arg Ala Ala Thr Ala Ala Arg
                85                  90                  95

Leu Pro Ala Pro Pro Ala Pro Gln Pro Pro Ser Pro Thr Pro Ser
            100                 105                 110

Pro Pro Arg Pro Thr Leu Ala Arg Glu Asp Asn Glu Glu Asp Glu Asp
        115                 120                 125

Glu Pro Thr Glu Thr Glu Thr Ser Gly Glu Gln Leu Gly Ile Ser Asp
    130                 135                 140

Asn Gly Gly Leu Phe Val Met Asp Glu Asp Ala Thr Leu Gln Asp Leu
145                 150                 155                 160

Pro Pro Phe Cys Glu Ser Asp Pro Glu Ser Thr Asp Asp Gly Ser Leu
                165                 170                 175

Ser Glu Glu Thr Pro Ala Gly Pro Pro Thr Cys Ser Val Pro Pro Ala
            180                 185                 190

Ser Ala Leu Pro Thr Gln Gln Tyr Ala Lys Ser Leu Pro Val Ser Val
        195                 200                 205

Pro Val Trp Gly Phe Lys Glu Lys Arg Thr Glu Ala Arg Ser Ser Asp
    210                 215                 220

Gly Glu Asn Gly Pro Pro Ser Pro Ser Pro Asp Leu Asp Arg Ile Ala Ala
225                 230                 235                 240
```

```
Ser Met Arg Ala Leu Val Leu Arg Glu Ala Glu Asp Thr Gln Val Phe
            245                 250                 255

Gly Asp Leu Pro Arg Pro Arg Leu Asn Thr Ser Asp Phe Gln Lys Leu
            260                 265                 270

Lys Arg Lys Tyr
            275

<210> SEQ ID NO 3
<211> LENGTH: 256
<212> TYPE: PRT
<213> ORGANISM: Homo sapiens

<400> SEQUENCE: 3

Met Ala Ser Gly Arg Pro Glu Glu Leu Trp Glu Ala Val Val Gly Ala
  1               5                  10                  15

Ala Glu Arg Phe Arg Ala Arg Thr Gly Thr Glu Leu Val Leu Leu Thr
             20                  25                  30

Ala Ala Pro Pro Pro Pro Arg Pro Gly Pro Cys Ala Tyr Ala Ala
         35                  40                  45

His Gly Arg Gly Ala Leu Ala Glu Ala Ala Arg Cys Leu His Asp
     50                  55                  60

Ile Ala Leu Ala His Arg Ala Ala Thr Ala Ala Arg Leu Pro Ala Pro
 65                  70                  75                  80

Pro Pro Ala Pro Gln Pro Pro Ser Pro Thr Pro Ser Pro Pro Arg Pro
             85                  90                  95

Thr Leu Ala Arg Glu Asp Asn Glu Glu Asp Glu Asp Glu Pro Thr Glu
            100                 105                 110

Thr Glu Thr Ser Gly Glu Gln Leu Gly Ile Ser Asp Asn Gly Gly Leu
            115                 120                 125

Phe Val Met Asp Glu Asp Ala Thr Leu Gln Asp Leu Pro Pro Phe Cys
130                 135                 140

Glu Ser Asp Pro Glu Ser Thr Asp Asp Gly Ser Leu Ser Glu Glu Thr
145                 150                 155                 160

Pro Ala Gly Pro Pro Thr Cys Ser Val Pro Ala Ser Ala Leu Pro
            165                 170                 175

Thr Gln Gln Tyr Ala Lys Ser Leu Pro Val Ser Val Pro Val Trp Gly
            180                 185                 190

Phe Lys Glu Lys Arg Thr Glu Ala Arg Ser Ser Asp Gly Glu Asn Gly
            195                 200                 205

Pro Pro Ser Ser Pro Asp Leu Asp Arg Ile Ala Ala Ser Met Arg Ala
            210                 215                 220

Leu Val Leu Arg Glu Ala Glu Asp Thr Gln Val Phe Gly Asp Leu Pro
225                 230                 235                 240

Arg Pro Arg Leu Asn Thr Ser Asp Phe Gln Lys Leu Lys Arg Lys Tyr
            245                 250                 255

<210> SEQ ID NO 4
<211> LENGTH: 20
<212> TYPE: DNA
<213> ORGANISM: Homo sapiens

<400> SEQUENCE: 4
tcaccgccct caaaagacat                                          20

<210> SEQ ID NO 5
<211> LENGTH: 20
<212> TYPE: DNA
```

```
<213> ORGANISM: Homo sapiens

<400> SEQUENCE: 5
tcggggcgcc ccgacgccat                                               20

<210> SEQ ID NO 6
<211> LENGTH: 10
<212> TYPE: DNA
<213> ORGANISM: Homo sapiens

<400> SEQUENCE: 6
gaaccaaccg                                                          10

<210> SEQ ID NO 7
<211> LENGTH: 10
<212> TYPE: DNA
<213> ORGANISM: Homo sapiens

<400> SEQUENCE: 7
tacaacgagg                                                          10

<210> SEQ ID NO 8
<211> LENGTH: 22
<212> TYPE: DNA
<213> ORGANISM: Homo sapiens

<400> SEQUENCE: 8
gggctctttg tgatggatga gg                                            22

<210> SEQ ID NO 9
<211> LENGTH: 20
<212> TYPE: DNA
<213> ORGANISM: Homo sapiens

<400> SEQUENCE: 9
ttgggaatgg gagacgcaag                                               20

<210> SEQ ID NO 10
<211> LENGTH: 19
<212> TYPE: DNA
<213> ORGANISM: Homo sapiens

<400> SEQUENCE: 10
aaggagaaga ggacagagg                                                19
```

PROGNOSTIC COMPOSITIONS FOR PROSTATE CANCER AND METHODS OF USE THEREOF

This application claims priority under 35 U.S.C §119 (e) to U.S. Provisional application No. 60/055,285 filed on Aug. 13 1997, the disclosure of which is incorporated herein by reference.

FIELD OF THE INVENTION

This invention relates to the field of prostate cancer detection. More specifically, novel compositions are provided which serve as prognostic indicators for late stage disease. Methods are also provided which facilitate the identification of those patients at risk for aggressive prostate cancer progression.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

This year prostate cancer is expected to be diagnosed in 200,000 men in the U.S. and to result in the loss of 38,000 lives. Such numbers make prostate cancer the most frequently diagnosed malignancy (other than that of the skin) in American males and the second leading cause of cancer-related death in that group. Physicians usually detect cancers by finding a lump in the prostate gland, which is a walnut shaped structure that helps to maintain the viability of sperm. Such lumps may be discovered during a routine checkup or an examination prompted by a patient's complaint of sudden urinary discomfort, or occasional impotence.

In some instances, prostate cancer is detected in the course of treatment for a disorder called benign prostatic hyperplasia. This condition, an aging-related enlargement of the prostate, affects more than half of all men older than 45 and gives rise (albeit more gradually) to the same urinary troubles caused by a prostate tumor. If the symptoms become too troublesome, a transurethral resection of the prostate, a process whereby parts of the gland are scraped away may be performed. Whenever resection is done, the excised tissue is analyzed under a microscope for evidence of malignancy, which is occasionally found.

A simple blood test for prostate specific antigen (PSA) constitutes a third means of detecting prostate cancer. Increased PSA levels can signal the presence of cancer in individuals who display no symptoms of prostate abnormalities.

Most prostate cancer (CaP) patients have no known risk factors for tumor development or rate of disease progression. The present inventors have appreciated the need for molecular markers for prostate cancer progression to identify patients who are at risk for aggressive disease and would benefit from early treatment.

SUMMARY OF THE INVENTION

This invention provides novel biological molecules useful for identification, detection and/or regulation of complex signaling events involved in prostate cancer progression. According to one aspect of the present invention, an isolated double stranded nucleic acid molecule, CLAR1, is provided which encodes a protein between about 250 and about 300 amino acids in length (preferably about 276 amino acids) that is a late stage specific marker for prostate cancer progression. The protein encoded by the CLAR1 nucleic acid molecule comprises a presently determined carboxy-terminal serine phosphorylation site and at least one or a multiplicity of SH3 binding domains. In a particularly preferred embodiment, the CLAR1 marker protein has an amino acid sequence of SEQ ID NO: 2. An exemplary nucleic acid molecule of the invention is set forth in SEQ ID NO: 1.

According to another aspect of the present invention, an isolated nucleic acid molecule is provided, which has a sequence selected from the group consisting of: (1) SEQ ID NO: 1; (2) a sequence which hybridizes with SEQ ID NO: 1; 3) a nucleic acid sequence encoding a polypeptide of SEQ ID NO: 2; 4) a nucleic acid sequence encoding a polypeptide of SEQ ID NO: 3; and 5) a natural allelic variant of a sequence of 1), 2), 3) or 4).

According to another aspect of the present invention, an isolated late stage-specific prostate cancer progression marker protein is provided which has a deduced molecular weight of between about 30 kDa and 50 kDa (preferably between about 30 kDa and 40 kDa and most preferably 33.8 kDa). In a preferred embodiment of the invention, the protein is of human origin, and has an amino acid sequence which is the same as or substantially the same as SEQ ID NO: 2. In yet another embodiment, the polypeptide may be derived from an alternatively spliced CLAR1 mRNA molecule and has a sequence the same as or substantially the same as SEQ ID NO: 3.

A further aspect of the present invention provides an oligonucleotide or polynucleotide fragment of the nucleotide sequence shown in SEQ ID NO: 1 or a complementary sequence thereof, in particular, for use in a method of obtaining and/or screening nucleic acid.

According to another aspect of the present invention, antibody binding domains or antibodies immunologically specific for the proteins described hereinabove are provided.

Various terms relating to the biological molecules of the present invention are used hereinabove and also throughout the specifications and claims. The terms "specifically hybridizing," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism in which it originated. For example, the "isolated nucleic acid" may comprise a DNA molecule inserted into a vector, such as a plasmid or virus vector, or integrated into the genomic DNA of a prokaryote or eukaryote. A nucleic acid molecule of the present invention may be single or double stranded.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein.

This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight of a given compound (e.g., nucleic acid, oligonucleotide, protein, etc.). More preferably, the preparation comprises at least 75% by weight, and most preferably 90–99% by weight of the given compound. Purity is measured by methods appropriate for the given compound (e.g. chromatographic methods, agarose or polyacrylamide gel electrophoresis, HPLC analysis, and the like). "Isolated is not meant to exclude artificial or synthetic mixtures with other compounds, or the presence of impurities which do not interfere with biological activity, and which may be present, for example, due to incomplete purification, addition of stabilizers, or compounding into pharmaceutically acceptable preparations.

With respect to antibodies of the invention, the term "immunologically specific" refers to antibodies that bind to one or more epitopes of a protein of interest (e.g., CLAR1), but which do not substantially recognize and specifically bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

An oligonucleotide is preferably at least 10 nucleotides in length, more preferably at least 15 nucleotides in length, most preferably at least 20 nucleotides in length.

The present invention also includes active portions, fragments, derivatives and functional mimetics of the CLAR1 polypeptide or protein of the invention.

An "active portion" of CLAR1 polypeptide means a peptide which is less than said full length CLAR1 polypeptide, but which retains its essential biological activity.

A "fragment" of the CLAR1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the CLAR1 polypeptide sequence, antigenic determinants or epitopes are useful for raising antibodies to a portion of the CLAR1 amino acid sequence.

A "derivative" of the CLAR1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wildtype CLAR1 polypeptide.

"Functional mimetic" means a substance which may not contain an active portion of the CLAR1 amino acid sequence, and probably is not a peptide at all, but which retains the essential biological activity of natural CLAR1 polypeptide.

As outlined above, the CLAR1 polypeptide or protein of the invention includes any analogue, fragment, derivative or mutant which is derived from a CLAR1 polypeptide and which retains at least one property of the CLAR1 polypeptide. Different "variants" of the CLAR1 polypeptide exist in nature. These variants may be allelic variations characterized by differences in the nucleotide sequences of the structural gene coding for the protein, or may involve different splicing or post-translational modification. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the CLAR1 polypeptide, (c) variants in which one or more amino acids includes a substituent group, and (d) variants in which the CLAR1 polypeptide is fused with another polypeptide such as serum albumin. Other CLAR1 polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations etc), chemical, and enzymatic techniques that are known to the person having ordinary skill in the art.

If such allelic variations, analogues, fragments, derivatives, mutants, and modifications, including alternative mRNA splicing forms and alternative post-translational modification forms result in derivatives of the CLAR1 polypeptide which retain any of the biological properties of the CLAR1 polypeptide, they are included within the scope of this invention.

In a further aspect of the present invention, there is provided a kit for detecting CLAR1 nucleic acid according to the present invention associated with cancer, or a susceptibility to cancer, the kit comprising one or more nucleic acid probes capable of binding and/or detecting a CLAR1 nucleic acid. Alternatively, the kit may comprise one or more antibodies capable of specifically binding and/or detecting CLAR1 nucleic acid or protein or a pair of oligonucleotide primers having sequences corresponding to, or complementary to a portion of the nucleic acid sequence set out in SEQ ID NO: 1 for use in amplifying a CLAR1 nucleic acid by, for example, polymerase chain reaction (PCR).

In yet another aspect of the invention, transgenic animals, including CLAR1 knock-out animals, are provided which are useful for elucidating the role of CLAR1 plays in neonatal development and cancer progression.

There is currently a need for models of prostate cancer, including animal models, to enable screening and identification of compounds for the treatment of this disease. CLAR1 gene expression is changed during prostate cancer development and disease progression. A transgenic animal expressing the CLAR1 protein would provide a useful model in which to investigate cancer development, tumor progression, and therapeutic effects. Preferably, the transgenic animal expresses the CLAR1 protein at a level which is higher than the normal level of CLAR1 protein.

Generally speaking, the murines, namely mice, rats and guinea pigs, are the most widely used animal models for disease. They are easy to manipulate and inexpensive. Unfortunately, these small mammals are not always compatible with the intended application. Thus, they are not always representative of the human model and its metabolism. Closer to man, the chimpanzee is a test animal which is used in particular for detecting therapeutic agents and vaccines which are directed against AIDS and cancer. However, its very substantial cost constitutes a major and compelling handicap with regard to its use.

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

In a specific embodiment, a transgenic animal expresses CLAR1. This transgenic animal may be a mouse, rat, guinea pig, dog, cat, rabbit, simian, and the like.

The information may be foreign to the species of animal to which the recipient belongs, (i.e. exogenous) foreign only to the particular individual recipient (i.e. exogenous), or genetic information already possessed by the recipient. In the last case, the introduced gene may be differently expressed compared to the native endogenous gene.

The genes may be obtained by isolating them from genomic sources, by preparation of cDNAs from isolated RNA templates, by directed synthesis, or by some combination thereof.

A transgenic animal according to the invention can integrate the CLAR1 encoding DNA sequences into all its cells or only into a certain percentage of cells; in the latter case it would be termed mosaic. In general, the CLAR1 encoding DNA sequences are integrated into all the cells. The inserted DNA sequences according to the invention encode all, or an active part, of the CLAR1 protein or variant thereof.

To be expressed within the transgenic animal, a gene should be operably linked to a regulatory region. Regulatory regions, such as promoters, may be used to increase, decrease, regulate or designate to certain tissues or to certain stages of development the expression of a gene. The promoter need not be a naturally occurring promoter. The "transgenic non-human animal" of the invention are produced by introducing a "transgene" into the germline of the non-human animal. The methods enabling the introduction of DNA into cells are generally available and well-known in the art. Different methods of introducing transgenes could be used. Generally, the zygote is the best target for microinjection. The use of zygotes as a target for gene transfer has a major advantage. In most cases, the injected DNA will be incorporated into the host gene before the first cleavage (Brinster, et al., (1985) Proc. Nat. Acad. Sci. USA 82, 4438–4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. (1976) Proc. Nat. Acad. Sci. USA 73, 1260–1264). Efficient infection of the blastomeres is obtained by enzymatic treatment to remove the zone pellucida (Hogan, et al., (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al., (1985) Proc. Natl. Acad. Sci. USA 82, 6927–6931; Van der Putten et al., (1985) Proc. Nat. Acad. Sci. USA 82, 6148–6152). Transfection is easily and efficiently obtained by culturing the blastomeres on a monolayer of virus-producing cells (Van der Putten et al., (1985) Proc. Natl. Acad. Sci. USA 82, 6148–6152; Stewart et al, (1987) EMBO J. 6:383–388). Alternatively, infection can be performed at a later stage. Virus or virus-producing cells can be injected into the blastocoele (Jahner et al., (1982) Nature 298:623–628). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate into the offspring. In addition, it is also possible to introduce a transgene into the germ line, albeit with low efficiency, by intrauterine retroviral infection of the midgestation embryo (Jahner et al., (1982) Nature 298:623–628.).

A third type of target cell for transgene introduction is the embryonal stem cell (ES). ES cells are obtained from pre-implantation embryos cultured in vitro (Evans, M. J., et al., (1981) Nature 292, 154–156; Bradley, A., et al. (1984) Nature 309, 255–258; Gossler, et al., (1986) Proc. Natl. Acad Sci. USA 83, 9065–9060; and Robertson, et al., (1986) Nature 322, 445–448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) Science 240, 1468–1474).

The methods for evaluating the presence of the introduced DNA as well as its expression are readily available and well-known in the art. Such methods include, but are not limited to DNA (Southern) hybridization to detect the exogenous DNA polymerase chain reaction (PCR), polyacrylamide gel electrophoresis (PAGE) and Western blots to detect DNA, RNA and protein.

As used herein, a "transgene" is a DNA sequence introduced into the germline of a non-human animal by way of human intervention and genetic engineering.

The nucleic acids, proteins/polypeptides, peptides and antibodies of the present invention are useful as diagnostic and/or prognostic indicators for assessing patients at risk for aggressive prostate cancer. They may also be used as research tools and should facilitate the elucidation of the mechanistic action of the novel genetic and protein interactions involved in the progression of prostate cancer.

The present invention also provides nucleic acid molecules, proteins, polypeptides or antibodies, as defined above, for use in medical treatment and preferably for use in the preparation of a medicament for the treatment of cancer, in particular prostate cancer.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 5A is a representative northern blot. FIG. 5B is a graph illustrating the organ distribution of CLAR1 expression. FIG. 5C is a graph showing the ratio of the 2.0 vs the 2.6 kb CLAR1 transcripts in the organs examined.

FIGS. 6A and 6B show the predicted amino acid sequence of CLAR1 (FIG. 6A) and a schematic drawing of the CLAR1 cDNA molecule and its corresponding splice variants (FIG. 6B).

DETAILED DESCRIPTION OF THE INVENTION

Figure 1:
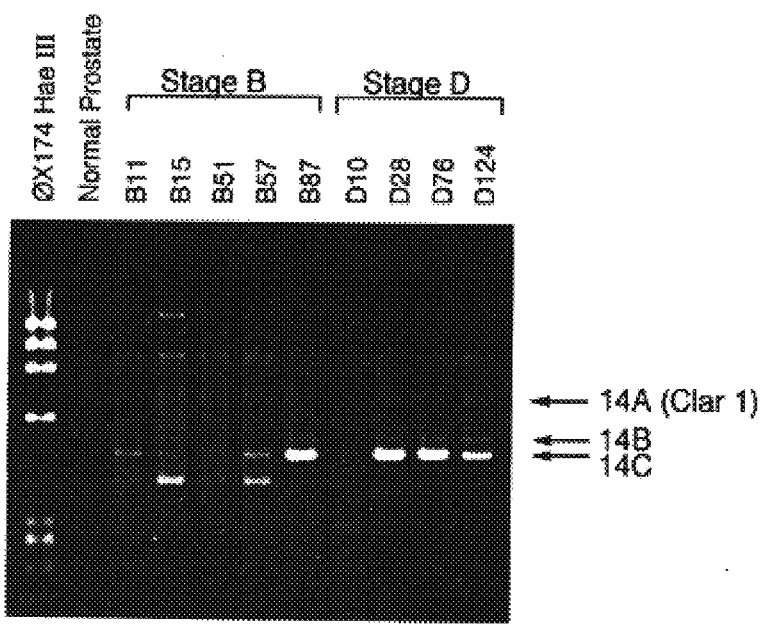
FIG. 1 is a photographed agarose gel showing differential display analysis of human primary prostate tumors.

Prostate cancer is the second leading cause of male cancer death in the United States (1). However, the etiology of this disease is unclear and most CaP patients have no known risk factors for CaP development or rate of progression. The progression of CaP to a systemic disease is controversial and two models have been presented (2). The first model suggests that CaP progression occurs from a well-differentiated, low volume, organ-confined disease (stages A, B & C) to a poorly differentiated, high volume, metastatic disease (stage D). The second model suggests that there are different types of CaP, some that progress as in the first model and others that progress early in their development, rapidly bypassing some stages toward metastatic disease. Indeed, there appears to be at least two different CaP patient populations in that some patients never progress, or do so very slowly, while others progress very rapidly.

The second CaP progression model is supported by a recent finding that 84% of non-palpable CaP cases identified by early screening methods were clinically significant tumors, with at least 44% of these significant tumors having already progressed to advanced cancers characterized by capsular penetration, lymph node and/or seminal vesicle involvement (3). By the time these tumors are palpable, many may have already progressed and will be beyond cure. While high Gleason grade tumors are associated with systemic disease, most prostate tumors are of moderate grade and the risk for the development of advanced disease is unpredictable (4).

There is an established precedence for gene expression changes within prostate cancers that correlate with grade and aggressive growth (5–7). The best examples are the e-cadherin/α-catenin genes which are significantly decreased in high Gleason grade human prostate tumors (6) and KAI1, a human metastasis suppressor gene for CaP (7).

It is very likely that significant gene expression differences exist between tumor types of the slow progressing and aggressive CaP patient populations. Therefore, the purpose of the experiments described below was to isolate molecular markers that will identify patients who are at risk for developing advanced CaP. A modified reverse-transcription PCR (RT-PCR) differential display method has been utilized (8) to screen non-metastatic and metastatic primary human prostate tumors for differences in gene expression patterns. A full-length cDNA to one of the differentially expressed marker fragments has been identified in accordance with the present invention. This cDNA represents a novel nucleic acid molecule which has been designated CLAR1 and is overexpressed in late stage human prostate tumors. In addition, the expression pattern of CLAR1 in primary human prostate tumors of various pathologic stage and Gleason grade, human CaP cell lines and in normal fetal and adult organs is described.

Molecular markers for CaP progression such as those described herein facilitate the identification of patients who are at risk for advanced disease. CLAR1 nucleic acids, proteins and specific antibodies may be used in a variety of prognostic and diagnostic screening methods to identify those patients who require aggressive treatment to inhibit prostate cancer progression.

I. Preparation of CLAR1-Encoding Nucleic Acid Molecules, CLAR1 Proteins, and Antibodies Thereto A. Nucleic Acid Molecules Nucleic acid molecules encoding the CLAR1 proteins of the invention may be prepared by two general methods: (1) They may be synthesized from appropriate nucleotide triphosphates, or (2) they may be obtained from biological sources. Both methods utilize protocols well known in the art.

The availability of nucleotide sequence information, such as the full length cDNA having SEQ ID NO: 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.6 kb double-stranded molecule may be synthesized as several smaller segments of appropriate complementarity. Complementary segments produced may then be annealed such that each segment possesses appropriate cohesive termini for attachment of an adjacent segment. Adjacent segments may be ligated by annealing cohesive termini in the presence of DNA ligase to construct an entire 2.6 kb double-stranded molecule. A synthetic DNA molecule so constructed may then be cloned and amplified in an appropriate vector.

Nucleic acid sequences encoding CLAR1 may be isolated from appropriate biological sources using methods known in the art. In a preferred embodiment, a cDNA clone is isolated from an expression library of human origin. In an alternative embodiment, genomic clones encoding CLAR1 may be isolated. Alternatively, cDNA or genomic clones encoding CLAR1 from other animal species may be obtained.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (22) using a hybridization solution comprising: 5×SSC, 5×Denhardt's reagent, 0.5–1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$T_m = 81.5°$ C. $+16.6$ Log[Na+]$+0.41$(% G+C)$-0.63$(% formamide)$-600/\#$bp in duplex.

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable E. coli host cell.

CLAR1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1. Such oligonucleotides are useful as probes for detecting or isolating CLAR1 genes or homologues in other species.

The nucleic acid sequences referred to above may be modified by addition, substitution, insertion or deletion of one or more nucleotides, but preferably without abolition of ability to hybridize selectively with nucleic acid with the sequence shown in SEQ ID NO: 1 or its complementary sequence, that is wherein the degree of homology of the oligonucleotide or polynucleotide with one of the sequences given is sufficiently high.

In some preferred embodiments, oligonucleotides according to the present invention that are fragments of the sequence shown in SEQ ID NO: 1 or complementary sequence, or allele associated with cancer susceptibility, are at least about 10 nucleotides in length, more preferably at least 15 nucleotides in length, most preferably at least about 20 nucleotides in length. The design of oligonucleotides is well within the capabilities of the skilled person. Preferred oligonucleotides are between 10 and 100 nucleotide bases in length. Such fragments individually represent aspects of the present invention.

Fragments and other oligonucleotides may be used as primers or probes as discussed but may also be generated (e.g. by PCR) in methods concerned with determining the presence in a test sample of a sequence indicative of cancer susceptibility.

Methods involving the use of nucleic acid in diagnostic and/or prognostic contexts, or for instance in determining susceptibility to cancer, and other methods concerned with determining the presence of sequences indicative of cancer susceptibility are discussed below.

Such oligonucleotide probes or primers, as well as the full-length sequence (and mutants, alleles, variants and derivatives) are also useful in screening a test sample containing nucleic acid for the presence of CLAR1, alleles, mutants or variants thereof, especially those that indicate susceptibility or predisposition to cancers, the probes hybridizing with a target sequence from a sample obtained from the individual being tested. The conditions of the hybridization can be controlled to minimize non-specific binding, and preferably stringent to moderately stringent hybridization conditions are preferred. The skilled person is readily able to design such probes, label them and devise suitable conditions for the hybridization reactions, assisted by textbooks such as Sambrook et al (1989) and Ausubel et al (1992).

On the basis of amino acid sequence information (SEQ ID NO: 2 or SEQ ID NO: 3) oligonucleotide probes or primers may be designed, taking into account the degeneracy of the genetic code. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more then 18 to 20. Those skilled in the art are well versed in the design of primers for use in processes such as PCR.

Nucleic acid according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled, e.g. chemically.

A convenient way of producing a polypeptide according to the present invention is to express nucleic acid encoding it, by use of the nucleic acid in an expression system. This is discussed below. Vectors comprising the nucleic acid of the present invention and host cells containing such vectors and/or nucleic acid according to the invention form further aspects of the present invention.

A host cell containing nucleic acid according to the present invention, e.g. as a result of introduction of the nucleic acid into the cell or into an ancestor of the cell and/or genetic alteration of the sequence endogenous to the cell or ancestor (which introduction may take place in vitro or in vivo), may be comprised (e.g. in the soma) within an organism which is an animal, particularly a mammal, which may be human or non-human, such as a rabbit, cat, dog, pig etc, or which is a bird such as a chicken. Genetically modified or transgenic animals or birds comprising such a cell are also provided as further aspects of the present invention.

The transgenic animals of the present invention may be used as animal disease models to assess therapeutic agents that may be efficacious in the treatment of cancer. However, such modified or transgenic animals are probably more useful in terms of research, particularly genetically modified animals wherein the modification is the deletion (knock-out) or mutation of nucleic acid corresponding to CLAR1 or an allele thereof.

B. Proteins

A full-length CLAR1 protein of the present invention may be prepared in a variety of ways, according to known methods. The protein may be purified from appropriate sources, e.g., human or animal cultured cells or tissues, by immunoaffinity purification.

The availability of nucleic acid molecules encoding CLAR1 or splice variants thereof enables production of the encoded proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of CLAR1 may be produced by expression in a suitable prokaryotic or eukaryotic system. For example, part or all of a DNA molecule, such as the cDNA having SEQ ID NO: 1, may be inserted into a plasmid vector adapted for expression in a bacterial cell, such as *Escherichia coli*, Saccharomyces cerevisiae or into a baculovirus vector for expression in insect cells. Such vectors comprise the regulatory elements necessary for expression of the DNA in the host cell (e.g. *E. coli* or insect cell), positioned in such a manner as to permit expression of the DNA in the host cell. Such regulatory elements required for expression include promoter sequences, transcription initiation and termination sequences, and, optionally, enhancer sequences.

The CLAR1 protein produced by nucleic acid expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. In yet another embodiment, GST fusion proteins may be employed to facilitate purification. Such methods are commonly used by those experienced in the field of recombinant protein purification.

The CLAR1 proteins of the invention, prepared by the aforementioned methods, may be analyzed according to standard procedures. For example, such proteins may be subjected to amino acid sequence analysis, and/or gel electrophoresis.

As discussed above, the present invention also provides CLAR1 polypeptides, or fragments or active portions thereof, for use in pharmaceuticals, in the development of drugs, diagnostic kits and for further study into its properties and role in vivo.

Polypeptides which are amino acid sequence variants, alleles, derivatives or mutants are also provided by the present invention. A polypeptide that is a variant, allele, derivative or mutant may have an amino acid sequence which differs from that given in SEQ ID NO: 2 or SEQ ID NO: 3 by one or more of addition, substitution, deletion and insertion of one or more amino acids. Preferred such polypeptides have CLAR1 function, that is to say have one or more of the following properties: immunological cross-reactivity with an antibody reactive with the polypeptides for which the sequence is set out in SEQ ID NO: 2 or SEQ ID NO: 3 respectively; and sharing an epitope with the polypeptides for which the amino acid sequence is set out in SEQ ID NO: 2 or SEQ ID NO: 3 respectively (as determined, for example, by immunological cross-reactivity between the two polypeptides).

A polypeptide which is an amino acid sequence variant, allele, derivative or mutant of the amino acid sequence shown in SEQ ID NO: 2 or SEQ ID NO: 3 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5–10, 10–20, 20–30, 30–40, 40–50, 50–100, 100–150, or more than 150 amino acids. A formula for determining % identity is set forth on page 12 of the present specification.

A polypeptide according to the present invention may be used in screening for molecules which affect or modulate its activity or function. Such molecules may be useful in a therapeutic (possibly including prophylactic) context.

The present invention also provides antibodies capable of immunospecifically binding to proteins of the invention. Polyclonal antibodies directed toward CLAR1 may be prepared according to standard methods. In a preferred embodiment, monoclonal antibodies are prepared, which react immunospecifically with various epitopes of CLAR1. Monoclonal antibodies may be prepared according to general methods of Köhler and Milstein, following standard protocols. Polyclonal or monoclonal antibodies that immunospecifically interact with CLAR1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-CLAR1 antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

II. Uses of CLAR1-Encoding Nucleic Acids, CLAR1 Proteins and Antibodies Thereto

The need for identifying those at risk for aggressive prostate cancer progression is great. To date, reliable prognostic indicators of tumor aggressiveness have not been available. The present invention provides nucleic acid sequences for use in genetic screening methods which facilitate the identification of those prostate cancer patients in need of aggressive treatment. CLAR1 proteins of the invention may also be used as a research tool to identify other proteins that are intimately involved in the aberrant genetic pathway that leads to prostate cancer progression.

A. CLAR1-Encoding Nucleic Acids

CLAR1-encoding nucleic acids may be used for a variety of purposes in accordance with the present invention. CLAR1-encoding DNA, RNA, or fragments thereof may be used as probes to detect the presence of and/or expression of genes encoding CLAR1 protein. Methods in which CLAR1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The CLAR1-encoding nucleic acids of the invention may also be utilized as probes to identify related genes from other species as demonstrated herein. As is well known in the art, hybridization stringencies may be adjusted to allow hybridization of nucleic acid probes with complementary sequences of varying degrees of homology. Thus, CLAR1-encoding nucleic acids may be used to advantage to identify and characterize other genes of varying degrees of relation to CLAR1, thereby enabling further characterization of the observed altered gene expression involved in the aggressive progression of prostate cancer. Additionally, they may be used to identify genes encoding proteins that interact with CLAR1 (e.g., by the "interaction trap" technique), which should further accelerate elucidation of these cellular signaling mechanisms which are involved in cancer progression (16).

Nucleic acid molecules, or fragments thereof, encoding CLAR1 may also be utilized to control the production of CLAR1, thereby regulating the amount of protein available to participate in disease signaling pathways. Alterations in the physiological amount of CLAR1 protein may act synergistically with other agents used to halt tumor progression. In one embodiment, the nucleic acid molecules of the invention may be used to decrease expression of CLAR1. In this embodiment, antisense molecules are employed which are targeted to expression-controlling sequences of CLAR1-encoding genes. Antisense oligonucleotides may be designed to hybridize to the complementary sequence of nucleic acid, pre-mRNA or mature mRNA, interfering with the production of polypeptide encoded by a given DNA sequence (e.g. either native CLAR1 polypeptide or a mutant or variant form thereof), so that its expression is reduced or prevented altogether. In addition to the CLAR1 coding sequence, antisense techniques can be used to target the control sequences of the CLAR1 gene, e.g. the 5' flanking sequence of the CLAR1 coding sequence such as the translation start site. Antisense oligomers should be sufficient length to hybridize to the target nucleotide sequence and exert the desired effect, e.g. blocking translation of a mRNA molecule. However, it should be noted that smaller oligomers are likely to be more efficiently taken up by cells in vivo such that a greater number of antisense oligomers may be delivered to the location of the target mRNA. Preferably, antisense oligomers should be at least 15 nucleotides long to achieve adequate specificity. Oligonucleotides for use in antisense technology are preferably between 15 to 30 nucleotides in length. The use of antisense molecules to decrease expression levels of a pre-determined gene is known in the art. The construction of antisense sequences and their use is described in Peyman and Ulman, Chemical Reviews, 90:543–584, (1990), Crooke, Ann. Rev. Pharmacol. Toxical., 32:329–376, (1992), and Zamecnik and Stephenson, P.N.A.S., 75:280–284, (1974). Examples of antisense sequences for the two spliced forms of CLAR1 (SEQ ID NO: 2 and SEQ ID NO: 3) include:

Full-length: 5' TCACCGCCCTCAAAAGACAT 3' (SEQ ID NO: 4) and

Shortened: 5' TCGGGGCGCCCCGACGCCAT 3' (SEQ ID NO: 5),respectively.

In another embodiment, overexpression of the CLAR1 gene is induced in a target population of cells to generate a co-suppression effect. This excess expression may act to promote downregulation of endogenous CLAR1 genes. In other cases, overexpression can lead to overproduction of the encoded protein, CLAR1. Overproduction of CLAR1 in cells may be assessed by immunofluorescence or any other standard technique known in the art. Alternatively, overexpression of CLAR1 by this method may facilitate the isolation and characterization of other components involved in the protein-protein complex formation that occurs as a cell progressively becomes more malignant.

As described above, CLAR1-encoding nucleic acids are also used to advantage to produce large quantities of substantially pure CLAR1 protein, or selected portions thereof.

B. CLAR1 Protein and Antibodies

Purified CLAR1, or fragments thereof, may be used to produce polyclonal or monoclonal antibodies which also may serve as sensitive detection reagents for the presence and accumulation of CLAR1 (or complexes containing CLAR1) in biopsy samples or cultured cells. Recombinant techniques enable expression of fusion proteins containing part or all of the CLAR1 protein. The full length protein or fragments of the protein may be used to advantage to generate an array of monoclonal antibodies specific for various epitopes of the protein, thereby providing even greater sensitivity for detection of the protein in prostate cells.

Polyclonal or monoclonal antibodies immunologically specific for CLAR1 may be used in a variety of assays designed to detect and quantitate the protein. Such assays include, but are not limited to: (1) flow cytometric analysis; (2) immunochemical localization of CLAR1 in prostate cells; and (3) immunoblot analysis (e.g., dot blot, Western blot) of extracts from prostate cells. Additionally, as described above, anti-CLAR1 can be used for purification of CLAR1 (e.g., affinity column purification, immunoprecipitation).

From the foregoing discussion, it can be seen that CLAR1-encoding nucleic acids, CLAR1 expressing vectors, CLAR1 proteins and anti-CLAR1 antibodies of the invention can be used to detect CLAR1 gene expression and alter CLAR1 protein accumulation for purposes of assessing those patients at risk for prostate progression. The invention also provides materials that facilitate the elucidation of the genetic and protein interactions involved in the regulation of the disease progression as a normal prostate cell gives rise to a malignant tumor. Exemplary approaches for detecting CLAR1 nucleic acid or polypeptides/proteins include:

a) determining the presence, in a sample from a patient, of nucleic acid according to the present invention; or b) determining the presence, in a sample from a patient, of the polypeptide encoded by the CLAR1 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from CLAR1 nucleic acid sequence; or, d) using a specific binding member capable of binding to a CLAR1 nucleic acid sequence, the specific binding member comprising nucleic acid hybridizable with the CLAR1 sequence, or substances comprising an antibody domain with specificity for a CLAR1 nucleic acid sequence or the polypeptide encoded by it, the specific binding member being labelled so that binding of the specific binding member to its binding partner is detectable; or, e) using PCR involving one or more primers based on CLAR1 nucleic acid sequences to screen for CLAR1 sequence in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the CLAR1 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the CLAR1 nucleic acid sequence and its association with cancer paves the way for aspects of the present invention to provide the use of materials and methods, such as are disclosed and discussed above, for establishing the presence or absence in a test sample of a variant form of the CLAR1 nucleic acid, in particular an allele or variant specifically associated with cancer, especially prostate cancer. This may be for diagnosing a predisposition of an individual to cancer. It may be for diagnosing cancer of a patient with the disease as being associated with CLAR1.

This allows for planning of appropriate therapeutic and/or prophylactic measures, permitting stream-lining of treatment. The approach further stream-lines treatment by targeting those patients most likely to benefit.

The present invention further provides "compositions" in biological compatible solution, pharmaceutically acceptable excipient, carrier, buffer, stabilizer or other materials well known to those skilled in the art, comprising the nucleic acids, polypeptides, vectors or antibodies of the invention. A biologically compatible solution is a solution in which the polypeptide, nucleic acid, vector, or antibody of the invention is maintained in an active form, e.g. in a form able to effect a biological activity. Generally, such a biologically compatible solution will be an aqueous buffer, e.g. Tris, phosphate, or HEPES buffer, containing salt ions. Usually the concentration of salt ions will be similar to physiological levels. Biologically compatible solutions may include stabilizing agents and preservatives.

Such compositions may be formulated for administration by topical, oral, parenteral, intranasal, subcutaneous, and intraocular routes. Parenteral administration is meant to include intravenous injection, intramuscular injection, intraarterial injection or infusion techniques. The compositions may be administered parenterally in dosage unit formulations containing standard well known non-toxic physiologically acceptable carriers, adjuvants and vehicles as desired.

The preferred sterile injectable preparations may be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or a mixture or such salts), Ringers solution, dextrose, water, sterile water, glycol, ethanol, and combinations thereof. 1,3-butanediol and sterile fixed oils are conveniently employed as solvents or suspending media. Any bland fixed oil may be employed including synthetic mono- or di-glycerides. Fatty acids such as oleic acid also find use in the preparation of injectables.

The composition medium may also be a hydrogel which is prepared from any biocompatible or non-cytotoxic (homo or hetero) polymer, such as a hydrophillic polyacrylic acid polymer that can act as a drug adsorbing sponge. Such polymers have been described, for example in applications WO93/08845, the entire contents of which are hereby incorporated by reference. Certain of them, such as, in particular, those obtained from ethylene and/or propylene oxide are commercially available. A hydrogel may be deposited directly onto the surface of the tissue treated, for example during surgical intervention.

The present invention provides "methods of treatment" which comprise the administration to a human or other animal of an effective amount of a composition of the invention.

Effective amounts vary, depending on the age, type and severity of the condition to be treated, body weight, desired duration of treatment, method of administration, and other parameters. Effective amounts are determined by a physician or other qualified medical professional.

Polypeptides according to the invention are generally administered in doses of about 0.01 mg/kg to about 100 mg/kg, preferably about 0.1 mg/kg to about 50mg/kg, and most preferably about 1 mg/kg to about 10 mg/kg of body weight per day.

The following examples are provided to illustrate various embodiments of the invention. They are illustrative only and do not limit the scope of the invention in any way.

EXAMPLE I

There is an established precedence for gene expression changes within prostate cancers that correlate with grade and aggressive growth (5–7). The best examples are the e-cadherin/α-catenin genes which are significantly decreased in high Gleason grade human prostate tumors (6) and KAI1, a human metastasis suppressor gene for CaP (7). It is very likely that significant gene expression differences exist between tumor types of the slow progressing and aggressive CaP patient populations. Molecular markers that will identify patients who are at risk for developing advanced CaP are provided herein. A modified reverse-transcription PCR (RT-PCR) differential display method (8) was employed to screen non-metastatic and metastatic primary human prostate tumors for differences in gene expression patterns. A full-length cDNA to one of the differentially expressed marker fragments was identified. This cDNA is derived from a novel gene which is referred to herein as CLAR1 and is overexpressed in late stage human prostate tumors. Methods are provided which enable the isolation and identification of this full-length cDNA for CLAR1. In addition, expression patterns of CLAR1 in primary human prostate tumors of various pathologic stage and Gleason grade, human CaP cell lines and in normal fetal and adult organs are disclosed.

Materials and Methods

Prostate Tumor Tissue and Total RNA Extraction

All tumor specimens were grossly dissected from surrounding normal tissue. Adjacent frozen sections of each tumor sample were stained with hematoxylin/eosin and reviewed by a pathologist. Tumor cells comprised at least 70% of each sample. Total RNA was extracted from the tumor tissues using guanidinium isothiocyanate as previously described (18). Ten μg of each RNA were treated with 2.5 units DNase (Promega) at 37□C. for 1 hour prior to northern analysis. cDNA was prepared using the SuperScript II Preamplification System (Gibco-BRL).

Differential Display and TA Cloning

Gene expression patterns between pathological stage B and stage D human prostate tumors were compared using a recently described modified differential display analysis (8). The degenerate decamer primers used to detect CLAR1 in the differential display analysis were: LG27: 5'GAAC-CAACCG3' (SEQ ID NO: 6) and LG 153: 5'TACAAC-GAGG3' (SEQ ID NO: 7). The PCR cycling conditions used were: 95° C., 5 minutes, then 45 cycles at 95° C., 1 minute; 34° C., 1 minute; 72° C., 1 minute with a final extension at 72° C., 10 minutes. The PCR products were resolved on 2.5% MetaPhor agarose (FMC), 1×TBE gels and were visualized with ethidium bromide. Stage-specific PCR marker fragments that were reproducible were isolated from the agarose gels using Qiaex II (Qiagen), subjected to a second PCR amplification using the same primer set and cloned into the TA Cloning vector, pCR II (Invitrogen). OneShot INVαF' competent cells (Invitrogen) were transformed with the TA vector-PCR fragment ligation products and selected on X-Gal plates in the presence of LB+50 μg/ml Ampicillin. At least five white colonies from each transformation were grown in 2×YT+50 μg/ml Kanamycin media overnight and plasmid DNA was isolated from these clones using the Perfect Prep system (5'→3'), the presence of the correct PCR fragment was verified by EcoR1 or BstXI (New England Biolabs) digestion and agarose gel electrophoresis. Clones containing the correct size insert were sequenced by automated fluorescent sequencing. The marker fragment inserts were isolated from the sequenced plasmid clones by EcoR1 or BstXI digestion, 1% NuSieve/GTG agarose gel electrophoresis and β-agarase I purification (New England Biolabs).

Northern Analysis of Human Prostate Tumors

Ten μg of total RNAs from 11 pathological stage B, 8 stage C and 5 stage D prostate tumors were separated on denaturing formaldehyde/1% SeaKem LE agarose gels and transferred onto Maximum Strength Nytran (Schleicher and Schuell). The 24 patient specimens were analyzed on three separate gels, for a total of 50 observations. Random-primed CLAR1 (differential display clone 14A1), desmin or β-actin probes were labeled with [α-$^{32}$P]dCTP (Redivue, 3000 Ci/mmol, Amersham) using a Multiprime DNA labeling system (Amersham). All probes were BioSpin-6 column-purified (Bio-Rad Laboratories).

The three blots containing the human prostate tumor RNAs were hybridized sequentially with the $^{32}$P-labeled probes to CLAR1, desmin and β-actin in Rapid-Hyb buffer (Amersham). Hybridization with CLAR1, β-actin and desmin probes was performed at 65° C., stringently washed in 2×SSC, 0.1% SDS at ambient temperature for 15 minutes followed by two washes in 0.2×SSC, 0.1% SDS at 65° C. for 15 minutes each. The blots were autoradiographed and scanned on a BAS 1000 phosphorimager (Fuji). Following each hybridization, the blots were washed in 55% formamide, 2×SSPE, 1% SDS at 65° C. for 1 hour, followed by a wash in 1×SSC, 0.1% SDS at 65° C. for 15 minutes to remove bound probe.

Cell Lines and Culture Conditions

All cell culture media and supplements were purchased from Gibco BRL. TSUPr1 and DU145 cells were cultured in DMEM supplemented with 10% fetal bovine serum, 50 units/ml penicillin and 50 μg/ml streptomycin. LNCaP cells were cultured in RPMI 1640 medium supplemented with 10% fetal bovine serum, 50 units/ml penicillin, 50 μg/ml streptomycin and 2 mM L-glutamine. PC-3 cells were cultured in F12K, Kaighn's modified medium supplemental with 10% fetal bovine serum, 50 units/ml penicillin and 50 μg/ml streptomycin. FNC 267β1 cells were cultured in Keratinocyte-SFM media supplemented with 50 μg/ml bovine pituitary extract and 5 ng/ml human epidermal growth factor, 50 units/ml penicillin and 50 μg/ml streptomycin. Total RNA was extracted from the exponentially growing cell lines using RNeasy (Qiagen) according to the manufacturer's protocol. Eight μg of each RNA were treated with 2.5 units DNase (Promega) at 37° C. for 1 hour prior to northern analysis.

Northern Analysis of Human Prostate Cell Lines and Normal Human Neonatal Prostate Cells Eight μg of DNase-treated total RNAs from the cell lines were separated on a denaturing formaldehyde/1% SeaKem LE agarose gel and transferred onto Maximum Strength Nytran. The blot was hybridized sequentially with random-primed, $^{32}$P-labeled probes to CLAR1 and β-actin and analyzed as described above.

Northern Analysis of Normal Human Organs

Human multiple organ northern blots (CLONTECH) that contain 2 μg of poly(A+) RNA from adult pancreas, kidney, skeletal muscle, liver, lung, placenta, brain, heart, peripheral blood leukocyte, colon, small intestine, ovary, testis, prostate, thymus, spleen and fetal kidney, liver, lung and brain were hybridized sequentially with random-primed, $^{32}$P labeled probes to CLAR1 and β-actin and analyzed as described above.

Quantitative CLAR1 RT-PCR Assay cDNA was prepared from 1 μg total RNA from primary human prostate tumors of various pathological stage and Gleason grade using Superscript II (Gibco BRL). The cDNAs were amplified using CLAR1 cDNA specific primers [CLAR1 Forward: 5'GGGCTCTTTGTGATGGAT- GAGG 3' (SEQ ID NO: 8) and CLAR1 Reverse: 5'TTGG-GAATGGGAGACGCAAG 3' (SEQ ID NO: 9)] at 0.1 µM primer concentration, 1×PCR Buffer II, 1.5 mM $MgCl_2$, 2 mM dNTPs and 0.6 units AmpliTaq (GeneAmp kit, Perkin-Elmer) at the following PCR cycling conditions: 94° C., 1 minute, 63° C., 1 minute and 72° C., 1 minute for 20 cycles. The 515 bp PCR products were analyzed on a 2% agarose/1×TBE gels and transferred to Maximum Strength Nytran. The Southern blots were hybridized with a random-primed, $^{32}$P-labeled probe derived from CLAR1, stringently washed and autoradiographed.

To normalize for equivalent amounts of cDNA added to the PCR assay, a quantitative RT-PCR assay was performed for cellular N-ras gene expression (10) (at the same reaction and cycling conditions as the CLAR1 RT-PCR with the exception that the number of cycles was increased to 25) followed by 2% agarose/1×TBE gel electrophoresis and Southern transfer to Maximum Strength Nytran. A c-N-ras oligo was end-labeled with [γ-$^{32}$P]ATP (Redivue, 5000 Ci/mmol, Amersham) using a 5' DNA Terminus Labeling system (Gibco BRL). The c-N-ras Southern blots were hybridized with the c-N-ras probe at 42° C., washed at low stringency in 2×SSC, 0.1% SDS at ambient temperature for 15 minutes twice, followed by a third wash in 0.2×SSC, 0.1% SDS at 42° C. for 15 minutes. Following the washes, the blots were exposed to autoradiographic film to detect the 299 bp c-N-ras PCR product. The average relative signal intensity of CLAR1 expression was quantitated by phosphorimage analysis (Fuji), following normalization to N-ras expression as described below. The RT-PCR quantitation assay was performed at least twice for each patient to verify the reproducibility of the CLAR1 expression level.

Relative CLAR1 Signal Intensity Calculation

To normalize for RNA loading on the northern blots or cDNA amount and amplification ability within the RT-PCR assay, the phosphorimage data of each sample (pixils/$mm^2$-background pixils $mm^2$) was divided by the corresponding β-actin (northerns) or c-N-ras (RT-PCR) phosphorimage data of each sample (pixils/$mm^2$-background pixils $mm^2$) to yield a ratio of CLAR1/β-actin or CLAR1/c-N-ras expression. The sample with the highest normalized CLAR1 ratio was assigned a relative signal intensity of 1.00 (100%). All other samples within the group were then divided by the CLAR1/β-actin or CLAR1/c-N-ras ratio of this highest expressing sample to produce a relative CLAR1 signal intensity for each sample analyzed.

Statistical Analyses

Statistical analyses on all relative CLAR1 signal intensity data were performed on a 486 IBM personal computer using the SPSS statistical software package for MS Windows 6.1. All data were first examined using the Levene Test for homogeneity of variance. The β-actin normalized average relative CLAR1 signal intensity data required non-parametric analyses. Therefore, the data were analyzed for statistical significance using Kruskal-Wallis one-way ANOVA, followed by Fisher's LSD posthoc comparisons. The c-N-ras normalized average relative CLAR1 signal intensity data were suitable for one-way ANOVA, followed by Mann-Whitney Wilcoxon Rank Sum posthoc comparisons. For all tests, the significance level was assigned at $p \leq 0.05$.

CLAR1 cDNA Isolation

The full-length CLAR1 cDNA was isolated from an adult human heart (female, 50 years old) cDNA library in pCMV-SPORT (Gibco BRL) using the GeneTrapper cDNA selection system (Gibco BRL) and following the manufacturer's instructions. The oligonucleotide primer 5' dAAGGAGAA-GAGGACAGAGG 3' (SEQ ID NO: 10) was used to isolate CLAR1-specific cDNA library clones. Briefly, the biotinylated oligonucleotide CLAR1 primer was hybridized to prepared single-stranded heart cDNA library sequences and isolated using streptavidin-coated paramagnetic beads and a magnetic separator. Following separation from the unhybridized library sequences, the probe-magnetic bead complex was removed from the single-stranded cDNA target sequences and the target sequences were repaired to double-stranded molecules using the non-biotinylated oligonucleotide CLAR1 primer identical to that used to select the target. Following repair, this enriched plasmid sequence pool was used to transform ElectroMAX DH10B cells (Gibco BRL). Colony blots were prepared from these CLAR1 cDNA-enriched transformation plates on Nytran circles (Schleicher & Schuell) and hybridized with a multi-primed, $^{32}$P-labeled probe that represented CLAR1 as described above. Positive colonies were selected from the plate and grown in overnight cultures. Plasmid DNA was then prepared and the cDNA sequences determined by automated fluorescent sequencing. Sequence data from the clones were analyzed using the MacVector software package. The open reading frame of CLAR1 as well as its predicted protein sequence were determined.

Chromosomal Location of CLAR1 Gene

Metaphase spreads from phytohemagglutinin-stimulated lymphocytes of a healthy female donor were prepared as described (13). The hybridization probe for chromosomal mapping was a 1.2 kb cDNA insert of 14A1.2 in pCMV-SPORT, a CLAR1 positive clone that was isolated from the human heart cDNA library described above. Fluorescent in situ hybridization (FISH) and detection of immunofluorescence were carried out as previously described (14). The probe was labeled with biotin-16-dUTP (Boehringer Mannheim) by nick translation, denatured and hybridized overnight at 37° C. under suppressive conditions since the insert contained some sequence from the 3' UTR. Hybridization sites were detected with fluorescein-labeled avidin (Oncor) and amplified by addition of anti-avidin antibody (Oncor) and a second layer of fluorescein-labeled avidin. The chromosome preparations were counterstained with diamidino-2-phenylindole (DAPI) and observed with a Zeiss Axiophot epifluorescence microscope equipped with a cooled charge coupled device camera (Photometrics) operated by a Macintosh computer workstation. Digitized images of DAPI staining and fluorescein signals were captured, pseudo-colored and merged using Oncor version 1.6 software.

Southern Analysis of CLAR1 Gene in Other Species

A Southern "zoo" blot was prepared that contained genomic DNA from human, cat, cow, dog, horse, mouse (Balb/c nude), pig, rat (Fisher) and yeast (*Schizosaccharomyces pombe*). Genomic DNA (5 µg) from each species was digested with EcoRI (New England BioLabs) and separated on a 0.8% agarose, 1×TBE gel and transferred onto a MagnaCharge membrane (Micron separations, Inc.). The blot was hybridized as described above with a $^{32}$P-labeled probe to CLAR1 at 42° C., washed twice in 2×SSC, 0.1% SDS, at ambient temperature, followed by a wash in 0.2×SSC, 0.1% SDS at 42° C. and autoradiographed.

Results

Differential Display Analysis

To identify CaP progression markers, gene expression patterns were compared between organ-confined (stage B) and metastatic (stage D) primary prostate tumors. Using a recently described, modified differential display technique (8), total RNAs from pathologic stage B and D prostate tumors were reverse-transcribed and amplified with multiple combinations of degenerate decamer primer sets. cDNA from each tumor RNA sample was amplified with 25–30 primer combinations using the Perkin-Elmer GeneAmp kit and 1 $\mu$M primer concentration. The resulting PCR products were analyzed on 2.5% MetaPhor/1×TBE agarose gels. RT-PCR reactions were performed three times to verify the reproducibility of suspected marker fragments. Representative results from one of three RT-PCR analyses from which CLAR1 was identified and isolated are shown in FIG. 1. The amplified 680 bp CLAR1 DNA fragment (initially denoted as clone 14A) that exhibited late stage-specificity is indicated by the arrow and was excised from the gel and cloned (11). Southern blot analysis of the RT-PCR products from which CLAR1 was isolated confirmed that the correct differentially expressed late stage fragment had been cloned (12).

Expression of CLAR1 in Human Prostate Cancer

To confirm the stage-specificity of the cloned differential display fragments, $^{32}$P-labeled, purified inserts from the sequenced clones were used to probe three independent northern blots containing total RNA from stage B, C and D human primary prostate tumors. Of 18 RT-PCR fragment clones tested, the stage-specificity of 3 clones were confirmed. One of these clones has been designated CLAR1. The CLAR1 probe detected two transcripts, approximately 2 and 2.6 kb in size, respectively. See FIG. 2. Both CLAR1-detected transcripts were significantly overexpressed in late stage (C) and D), advanced prostate tumors. Similar results were obtained following CLAR1 hybridization to two additional prostate tumor northern blots. The average relative signal intensities of the CLAR1 transcripts detected in the primary CaP tumor northern blots have been determined using phosphorimage analysis (Fuji). $\beta$-actin gene expression was simultaneously assessed to normalize for RNA loading. CLAR1 expression was significantly increased by 3–4 fold in stage C and D prostate tumors as compared to early stage B tumors.

Figure 2:
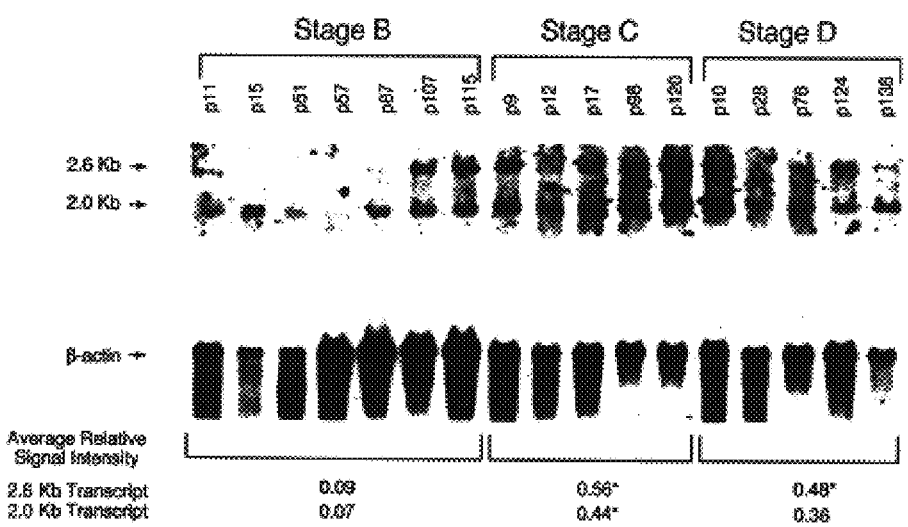
FIG. 2 is an autoradiograph depicting northern blot analysis of CLAR1 expression in pathological stage B, C and D primary human prostate tumors.
Figure 3A:
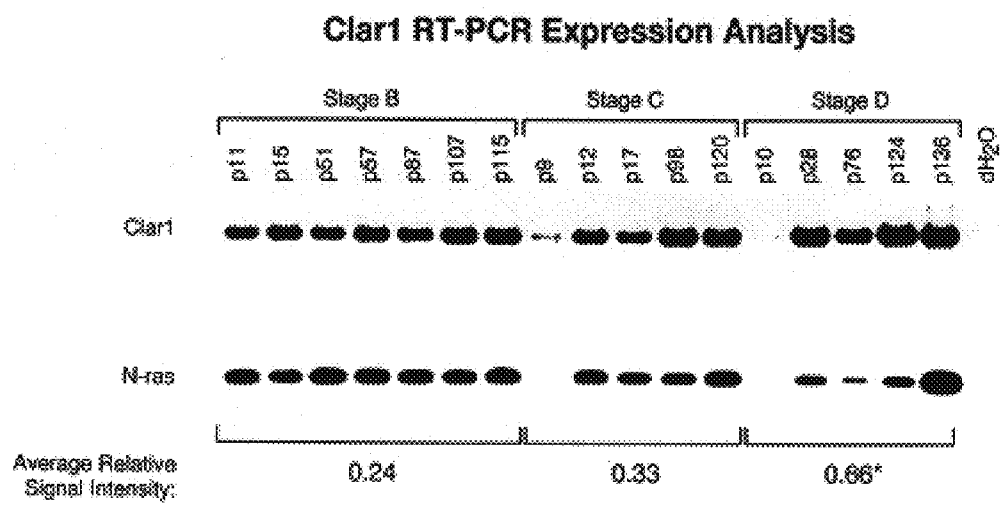
FIGS. 3A and 3B are autoradiographs showing quantitative RT-PCR analysis of CLAR1 in human primary prostate tumors of various pathological stage (FIG. 3A) and Gleason grade (FIG. 3B).
Figure 3B:
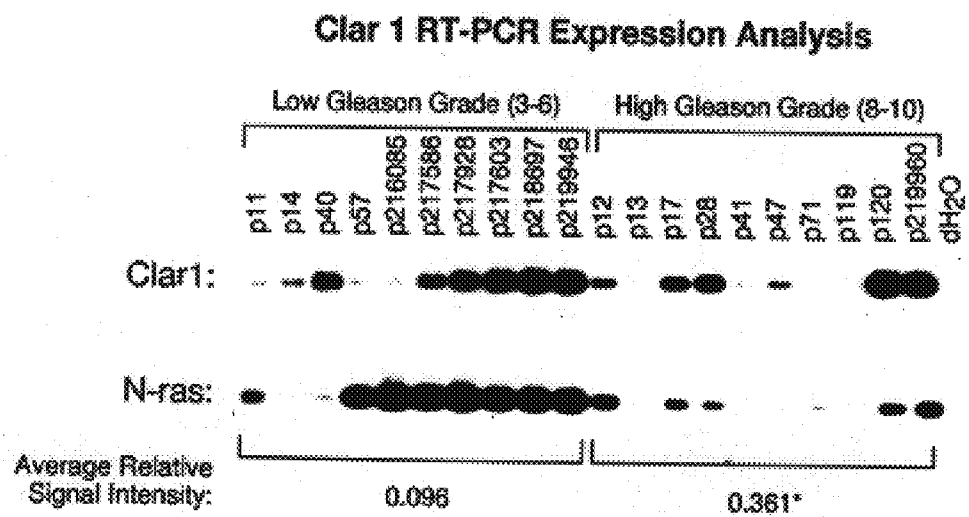

To be clinically useful, the expression level of the identified progression marker CLAR1 must be determined from small needle biopsy specimens. To this end, a quantitative RT-PCR assay has been developed that can be used on small samples to quantitate the level of CLAR1 gene expression within primary prostate tumors of various pathologic stage and Gleason grade. Using this RT-PCR assay, significant CLAR1 expression differences between stage B prostate tumors and stage C and D prostate tumors were detected (FIGS. 3A & B), similar to the results obtained with northern blot analysis (FIG. 2). In addition, the data demonstrate that CLAR1 expression was significantly increased by approximately 3-fold in prostate tumors of high Gleason grade (FIG. 3B).

Expression of CLAR1 in Human Prostate Cancer Cell Lines

Figure 4:
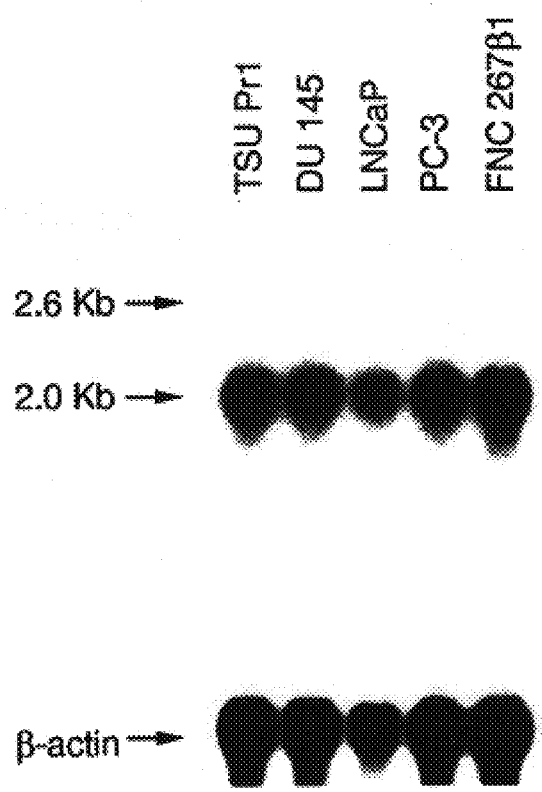
FIG. 4 is a northern blot demonstrating expression of CLAR1 in human prostate cancer and normal neonate prostate cell lines.

To investigate whether CLAR1 may also be expressed to high levels in human CaP cell lines that were derived from prostate tumor metastases, the expression pattern of CLAR1 in the TSU-Pr1, DU145, LNCaP and PC-3 cell lines as well as in FNC267$\beta$1, an immortalized normal neonatal prostate cell line was examined (15). Consistent with northern blot data on primary prostate tumors presented in FIG. 2, CLAR1 was expressed to high levels in all of the CaP cell lines examined. See FIG. 4. In addition, CLAR1 was expressed to similarly high levels in the neonatal prostate cells as well. Interestingly, all of these cell lines expressed increased levels of the 2.0 kB CLAR1 transcript (3.5–5.5 fold) compared to the 2.6 kB transcript, but the significance of this finding in unclear. See FIG. 5C. The expression of the late stage CaP marker in the neonate prostate cells is intriguing with regard to the high proliferative nature of both fetal tissue and tumor cells.

CLAR1 Expression in Fetal and Adult Human Organs

Figure 5A:
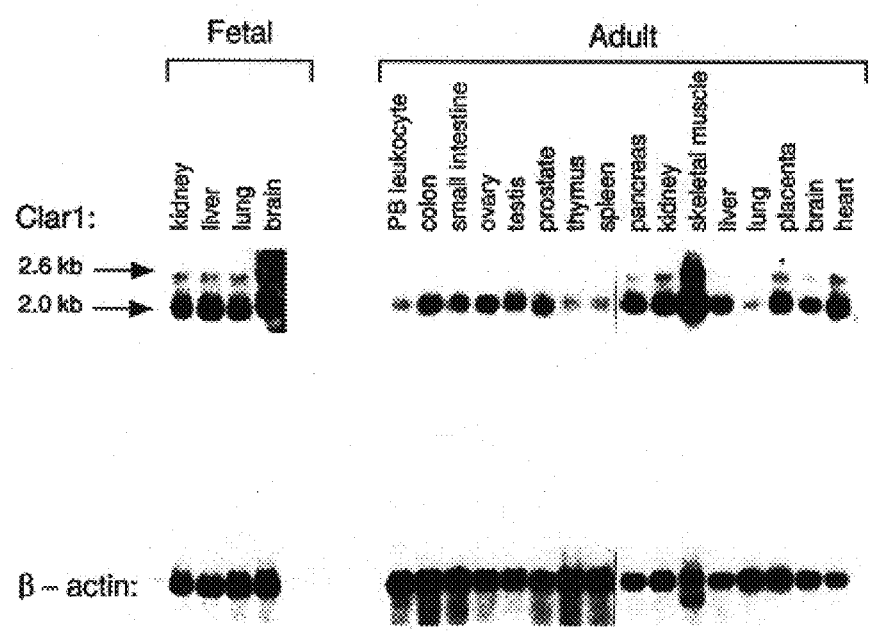
FIGS. 5A, 5B and 5C depict data obtained from northern blot analysis of CLAR1 expression in a variety of adult and fetal organs.
Figure 5B:
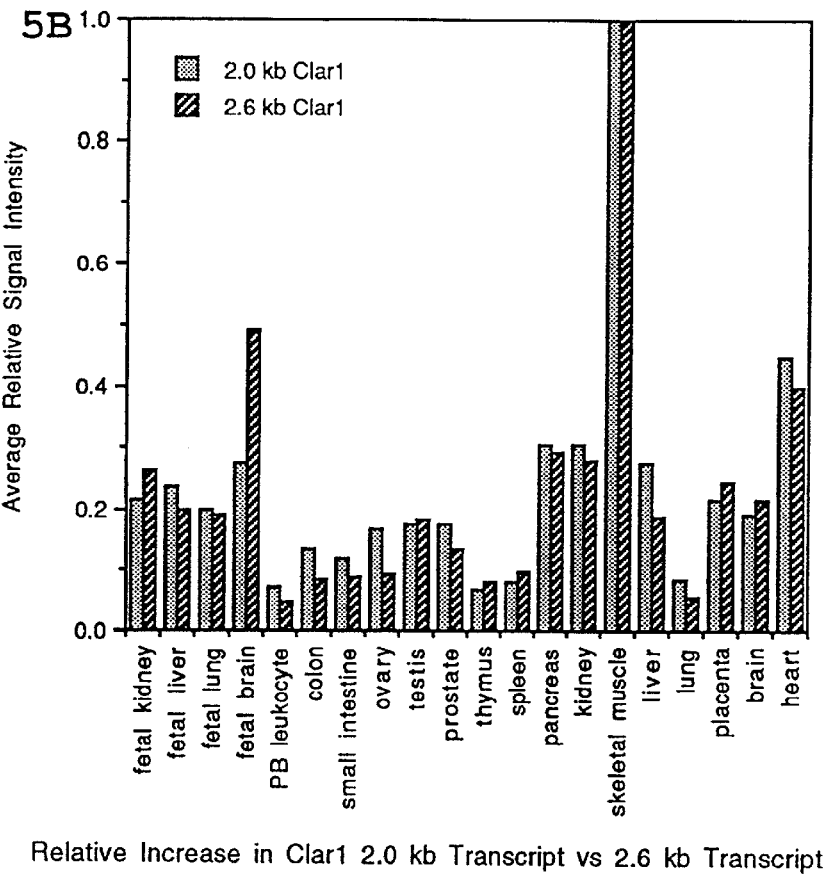
Figure 5C:
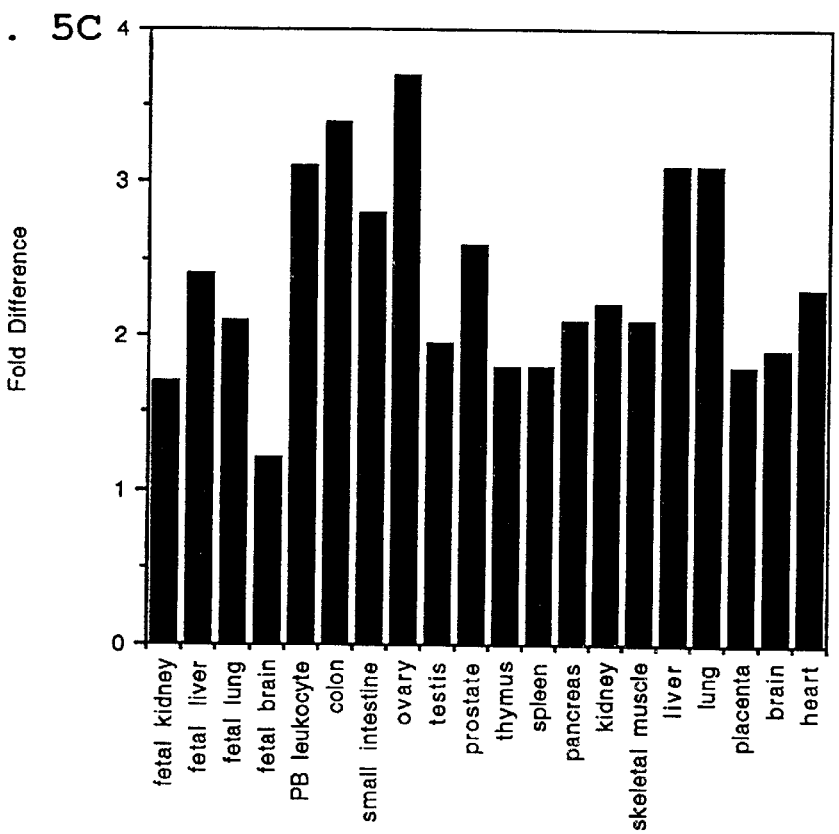

CLAR1 expression has been examined in fetal and adult normal human organs to determine the organ distribution of CLAR1 expression and the relative ratio of CLAR1 transcripts. Multiple organ northern blots containing poly(A+) RNA from several fetal and adult organs, including normal prostate were hybridized simultaneously with $^{32}$P-labeled probes to both CLAR1 and $\beta$-actin. See FIG. 5A. This approach allowed the direct comparison of CLAR1 expression in fetal and adult organs. FIG. 5A illustrates that CLAR1 expression, while detectable in all organs examined, exhibits highly variable transcript levels according to organ type. Fetal brain, adult skeletal muscle and heart have the highest signal relative to other normal organs. The remaining fetal organs and adult pancreas, kidney, liver, lung, and brain exhibited moderate CLAR1 expression. In all of the normal organs both CLAR1 transcripts were detected. However, the transcripts were not expressed at equivalent levels within each organ. See FIG. 5B. Expression appeared to be similar to that observed in the CaP cell lines and the neonate prostate cell line, wherein the 2.0 transcript was predominant (1.5–3.5 fold). While the significance of this change in transcript ratios remains to be determined, these changes are not as great as the ratio differences observed within the cell lines (3.5–5.5 fold) See FIG. 5C.

CLAR1 was expressed in normal prostate, albeit at moderately low levels. Since the prostate lane on the blot contains prostate RNA from 35 men, ranging in age from 21–70, (11), it is possible that this "normal" prostate lane may very well contain neoplastic foci from the older men within this group. Patient-matched normal prostate and prostates from young male organ donors must be evaluated to definitively determine the level of CLAR1 gene expression in normal prostate cells.

Skeletal muscle demonstrates relatively high CLAR1 expression (FIG. 5). Since skeletal and smooth muscle fibers are common within the fibromuscular stroma of the prostate (17), we assessed whether the high CLAR1 levels detected for stage C and D tumors (FIG. 2) simply reflected high muscle content rather than elevated CLAR1 expression within the cancer cells. The three northern blots containing the prostate tumor RNAs were rehybridized with a $^{32}$P-labeled probe to desmin which is expressed specifically in muscle. The data show that desmin RNA levels did not correlate with tumor stage (p=0.347), indicating that muscle content was not a confounding variable in the analysis of patient specimens (12).

Cloning and Characterization of CLAR1 cDNA

Based on the results of the organ expression analysis (FIGS. 5A, 5B and 5C), an adult human (female, 50 years old) heart SuperScript cDNA library cloned into pCMV-SPORT (Gibco-BRL) was screened using the GeneTrapper system (Gibco-BRL), following the manufacturer's instructions for the full-length cDNA to CLAR1. This system enriches for the CLAR1 sequence from the cDNA library, reducing the number of library clones that must be analyzed. Although expression of CLAR1 was highest in skeletal muscle, a compatible cDNA library for the GeneTrapper system was not available from this tissue source. The GeneTrapper screen of the adult human heart cDNA library resulted in 142 clones which were 14A-positive. Forty-six of the largest clones were sequenced by automated fluorescent sequencing. These experiments resulted in the identification of a 2.6 kb cDNA sequence encoding full length CLAR1. The full-length cDNA sequence encoding a splice variant of CLAR1 is set forth below (SEQ ID NO: 1):

```
GGCATAAGCCGGTCAGCTAAGGCCATGTTAATACGGGGCTGTCCCATCTCTCTGCGG

GGCGCGACAGCTGGAAGAGCCGAACGGATAATAGAAGAGGAGGGCGCGGATGGCGTC

GGGGCGCCCCGAGGAGCTGTGGGAGGCCGTGGTGGGGCCGCTGAGCGCTTCCGGGC

CCGGACTGGCACGGAGCTGGTGCTGCTGACCGCGGCCCCGCCGCCACCACCCCGCCC

GGGCCCCTGTGCCTATGCTGCCCATGGTCGAGGAGCCCTGGCGGAGGCAGCGCGCCG

TTGCCTCCACGACATCGCACTGGCCCACAGGGCTGCCACTGCTGCTCGGCTTCCTGC

GCCCCCACCAGCACCACAGCCACCCAGTCCCACACCCAGCCCACCCCGGCCTACCCT

GGCCAGAGAGGACAACGAGGAGGACGAGGATGAGCCCACAGAGACAGAGACCTCCGG

GGAGCAGCTGGGCATTAGTGATAATGGAGGGCTCTTTGTGATGGATGAGGACGCCAC

CCTCCAGGACCTTCCCCCCTTCTGTGAGTCAGACCCCGAGAGTACAGATGATGGCAG

CCTGAGCGAGGAGACCCCCGCCGGCCCCCCCACCTGCTCAGTGCCCCCAGCCTCAGC

CCTACCCACACAGCAGTACGCCAAGTCCCTGCCTGTGTCTGTGCCCGTCTGGGGCTT

CAAGGAGAAGAGGACAGAGGCGCGGTCATCAGATGGGGAGAATGGGCCGCCCTCTTC

GCCCGACCTGGACCGCATCGCGGCGAGCATGCGCGCGCTGGTGCTGCGAGAGGCCGA

GGACACCCAGGTCTTCGGGGACCTGCCACGGCCGCGGCTTAACACCAGCGACTTCCA

GAAGCTGAAGCGGAAATATTGAAGTCCAGGGAGGGAGCGCCCCGGGCCGCGTCCGCC

CCGTCCCACAATACGCCCCGCCCCACTCCCGGGGCCTGCTAATCTGAGGCCGATCC

GGGACCGGCCTCCTTGCGTCTCCCATTCCCAAGATTGTCCCGCCTCTGCCAATCCCC

GCCGTCCTTCCAGCCCACGACCTGCCGCGCCGAGGAGCGGCATCTGTCCCGTTTCCC

GATTGGGTCTGTCGTCTCTCCGCCTAGCGACAGATTCCTTCTATTAAGGGATTGG

CT6GCTGAGTTCTAAGCTCTAAATGGGTCAACTCCTTTGTTTTCCGCCTAGCGACAA

GGGATTTGCTCGCACGGCATTGGCTCCATCCCCTAGTCGCTGGACAGCTCTTTTTTT

GATTGGCTCAAATCCTGTAAAGGGCTTGACCAGTCTCTACATAGTCACCGTCCGCTT

TTCCTGAGTTCTCCCTCCCAATTGGCTCCAGCTTCCTGGGGGCGTGGCCAAGCCCTC

CTCTTCCCAGAATTGGCCCGGGGCCTTCAATTTACGTTTTTTACACTACGGGGACTG

GGGTTGTCTTTGCCCACGTCCCGACAAATTGTTCCCTGACCCCCTCAGGGATGGCCC

CAAACTGTCCCTGCCTCTGGCACCCCCTTTCATTGGTTCCATCCATCCCCACAACAG

CCTGCCAATCGAAGCCCGTCCCTGCATCCAGGATGGTACCAGTTCCCGCCCCTCGCC

CCCCACCTCCACAGGTGCCTTAAAGGGCCCTCGTCCACCCAAGGTGGGGGGCAGGGG

CCCTCACTTTCCGGCCCTGGTGTGGGGAGAGAGTGAGGGGTTGGGGGATCGGCAGT

TGGGAGGGGCGCTCTGAGATTAAAGAGTTTTACCTTTGGGGTAAAAAAAAAAAAAAA

AAAAAAAAAAAAAAAAAAAAAAAAAAAAAAAAAAAAAAAAAAAAAAAAAAAAAAAA

AAAAAAAAAA
```

The deduced amino acid sequence (SEQ ID NO: 2) encoded by the 2.6 kb CLAR1 cDNA is set forth hereinbelow and in FIG. 6A.

```
MSFEGGDGAG PAMLATGRAR MASGRPEELW EAVVGAAERF

RARTGTELVL LTAAPPPPPR PGPCAYAAHG RGALAEAARR

CLHDIALAHR AATAARLPAP PPAPQPPSPT PSPPRPTLAR
```

-continued
```
EDNEEDEDEP TETETSGEQL GISDNGGLFV MDEDATLQDL

PPFCESDPES TDDGSLSEET PAGPPTCSVP PASALPTQQY

AKSLPVSVPV WGFKEKRTEA RSSDGENGPP SSPDLDRIAA

SMRALVLREA EDTQVFGDLP RPRLNTSDFQ KLKRKY
```

In accordance with the present invention, it has been discovered that the CLAR1 message may be alternatively spliced (FIG. 6B) giving rise to a shorter deduced amino acid sequence which is set forth herein below as SEQ ID NO: 3:

```
MASGRPEELW EAVVGAAERF RARTGTELVL LTAAPPPPPR

PGPCAYAAHG RGALAEAARR CLHDIALAHR AATAARLPAP

PPAPQPPSPT PSPPRPTLAR EDNEEDEDEP TETETSGEQL

GISDNGGLFV MDEDATLQDL PPFCESDPES TDDGSLSEET

PAGPPTCSVP PASALPTQQY AKSLPVSVPV WGFKEKRTEA

RSSDGENGPP SSPDLDRIAA SMRALVLREA EDTQVFGDLP

RPRLNTSDFQ KLKRKY
```

The full length CLAR1 cDNA has a single open reading frame (nucleotides 811–1638) that predicts a protein of 276 amino acids with an approximate molecular mass of 33.8 kD (FIG. 6B). Alternative splicing of the message gives rise to a deduced amino acid sequence in which the first 20 amino acids are absent. The reading frame for both the full length and truncated CLAR1 proteins are the same. A BLAST search of the GenBank/EMBL, EST and SwissProt databases revealed that CLAR1 shares no significant sequence or protein homology with the exception of a CpG island within the protein.

The CLAR1 protein contains several PXXP sites which are consensus sequences for binding to SH3 domains. The presence of these sites suggests that the CLAR1 protein may function as a ligand for SH3 domain-containing proteins and may be involved in regulation or modification of these binding partners, many of which play significant roles within signal transduction pathways. In addition, the CLAR1 protein contains a PPSSP site near its C-terminus that may be a potential site for serine phosphorylation, indicating that the biochemical activity of CLAR1 may be regulated or influenced by serine phosphorylation. One function of the PXXP sites may be to bring CLAR1 together with this serine kinase for phosphorylation of the protein. The biochemistry of CLAR1 and the identity of its binding partners are currently being explored through yeast 2-hybrid analysis.

Chromosomal Localization of the CLAR1 Gene

Figure 7:
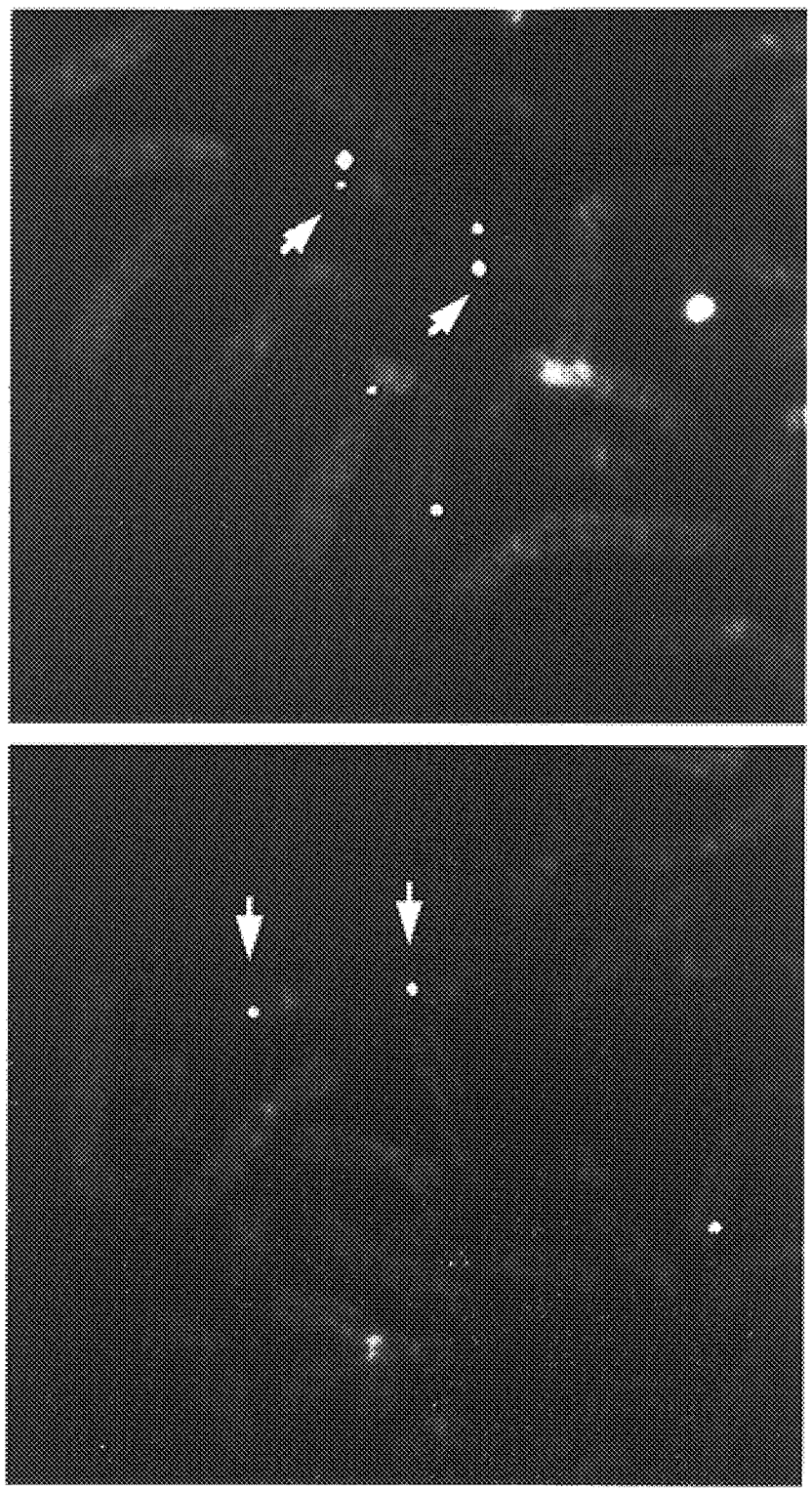
FIG. 7 depicts the results of chromosomal mapping of fluorescein-labeled 14A1.2 probe to chromosome 19q in human lymphocytes by FISH.

The chromosomal location of the CLAR1 gene was determined using fluorescent in situ hybridization (FISH) of a CLAR1-specific probe to human metaphase lymphocyte chromosomes. See FIG. 7. A GeneTrapper positive clone, 14A1.2 was used as a probe to hybridize to human metaphase spreads. Hybridization of the 14A1.2 probe revealed specific labeling on chromosome 19 with fluorescent signals detected on chromosome 19 in 20/21 metaphase spreads scored. Among 112 signals observed, 46 (41%) were on 19q and the distribution of signals was as follows: two chromatids (17 cells), four chromatids (3 cells). Overall, among 84 chromosome 19 chromatids scored, 46 (55%) exhibited hybridization to 19q. Signals localized to 19q13.3-q13.4, with most being located at band 19q13.3 (FIG. 7).

Conservation of the CLAR1 Gene Among Species

Figure 8:
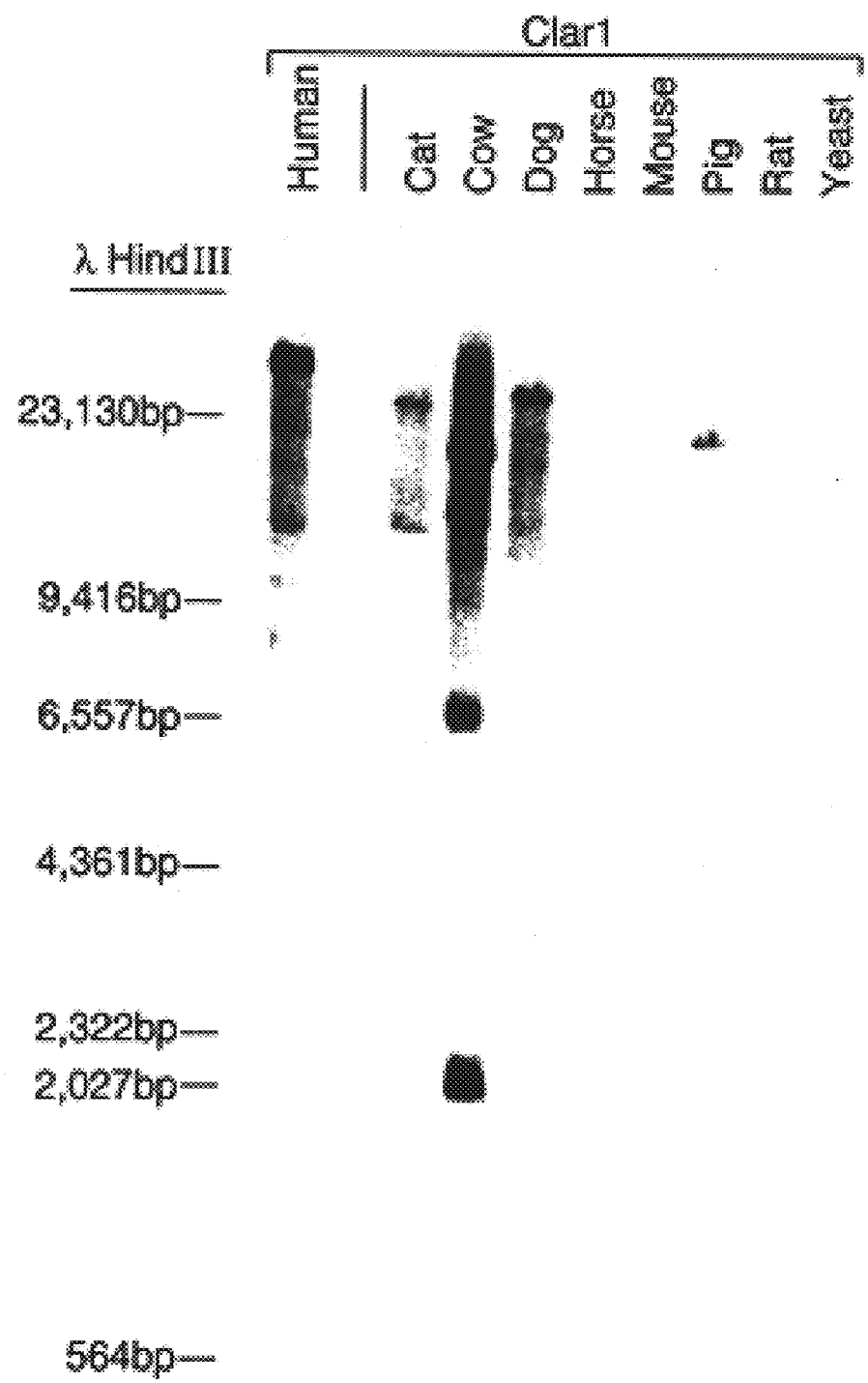
FIG. 8 is a Southern blot demonstrating the presence of CLAR1 in other species.

To determine the extent to which the CLAR1 gene is conserved among species, a Southern "zoo" blot containing human, cat, cow, dog, horse, mouse (Balb/c nude), pig, rat (Fisher) and yeast (*Schizosaccharomyces pombe*) genomic DNA was probed with a $^{32}$P-labeled probe of 14A1 (CLAR1). After autoradiography for 18 hours, the results revealed that the CLAR1 gene is well conserved among mammals, hybridizing most strongly with human and cow DNA, but also demonstrating visible bands in cat, dog, horse, mouse, pig and rat DNA. See FIG. 8. However, no hybridization signal was detected within yeast DNA, even upon a long (2 week) exposure. Thus, under the hybridization and wash conditions used, we were unable to detect a CLAR1 homologue in *S. pombe*. A search of the genome data base of *S. cerevisiae* was also performed. As in *S. pombe*, no CLAR1 homologue was found.

CLAR1 is a novel gene that represents a late stage-specific marker for CaP progression. While the effect of CLAR1 overexpression on CaP etiology and progression remains to be determined, the identification of this gene's role in the transformation of prostate epithelia into an aggressive, advanced adenocarcinoma will expand our understanding of this disease.

EXAMPLE II

The Immunohistochemical Detection of CLAR1 Expression in Prostate Biopsy Samples Prostate tissue core samples are collected from men suspected of having prostate cancer using an ultrasound guided biopsy method, and the tissue fixed in formulin. The tissue is then mounted on a glass slide and used for immunohistochemical analysis. Immunohistochemistry is performed using an antibody to CLAR1 and the signal is detected using a horseradish peroxidase (HRP) activity method (DAKO, Carpinteria, Calif.). Briefly, endogenous peroxidase activity is blocked with 3% peroxide/methanol, and antigen retrieval performed using the microwave method (2.5 min. at high power, 2×) in 10 mM citrate buffer, pH 7.6. Non-specific binding of the CLAR1 antibody will be blocked with 3% BSA/PBS/0.2% TritonX 100. ClAR1 protein is detected by treating with biotinylated secondary antibodies and washed n PBS/0.2% TritonX 100 (PBS/T). The slides are treated with a streptavidin-HRP complex for 10 min. and washed with PBS/T and counterstained with hematoxylin. The sections are examined for areas of malignancy and the presence and extent of CLAR1 expression in these areas is determined.

REFERENCES

1. Parker, S. L., T. Tong, S. Bolden and P. A. Wingo, 1996. Cancer Statistics, 1996. CA Cancer J. Clin., 46:5–27.
2. Whitmore, Jr., W. F., 1973. Cancer, 32:1104–1112.
3. Epstein, J. I., P. C. Walsh, M. Carmichael and C. B. Brendler, 1994. JAMA, 271:368–374.
4. Kramer, S. A., J. Spahr, C. B. Brendler, J. F. Glenn and D. F. Paulson, 1980. Experience with Gleason's histopathologic grading in prostatic cancer. J. Urol., 124:223–225.
5. Bussemakers, M. J. G., W. J. M. van de Ven, F. M. J. Debruyne and J. A. Schalken, 1991. Cancer Res., 51:606–611. Lee, W.-H., R. A. Morton, J. I. Epstein, J. D. Brooks, P. A. Campbell, G. S. Bova, W.-S. Hsieh, W. B. Isaacs and W. G. Nelson, 1994. Proc. Natl. Acad. Sci. U.S.A., 91:11733–11737. Foster, C. S., J. McLoughlin, I. Bashir and P. D. Abel, 1992. Hum. Pathol., 23:381–394. Bussemakers, M. J. C., G. W. C. T. Verhaegh, A. van Bokhoven, F. M. J. Debruyne and J. A. Schalken, 1992. Biochem. Biophys. Res. Comm., 182:1254–1259.
6. Umbas, R., J. A. Schalken, T. W. Aalders, B. S. Carter, H. F. M. Karthaus, H. E. Schaafsma, F. M. J. Debruyne and W. B. Isaacs, 1992. Cancer Res., 52:5104–5109. Umbas, R., W. B. Isaacs, P. P. Bringuier, H. E. Schaafsma, H. F. M. Karthaus, G. O. N. Oosterhof, F. M. J. Debruyne and J. A. Schalken, 1994. Cancer Res., 54:3929–3933. Bussemakers, M. J. G., R. J. A. van Moorselaar, L. A. Giroldi, T. Ichikawa, J. T. Isaacs, M. Takeichi, F. M. J. Debruyne and J. A. Schalken, 1992. Cancer Res., 52:2916–2922. Morton, R. A., C. M. Ewing, A. Nagafuchi, S. Tsukita and W. B. Isaacs, 1993. Cancer Res., 53:3585–3590.
7. Dong, J.-T., P. W. Lamb, C. W. Rinker-Schaeffer, J. Vukanovic, T. Ichikawa, J. T. Isaacs and J. C. Barrett, 1995. Science, 268:884–886.
8. Sokolav, B. P. and D. J. Prockop, 1994. Nucl. Acids Res., 22:4009–4015.
9. Tricoli, J. V., L. B. Rall, C. P. Karakousis, L. Herrera, N. J. Petrelli, G. I. Bell and T. B. Shows, 1986. Cancer Res., 46:6169–6173.
10. Tricoli, J. V., P. H. Gumerlock, J. L. Yao, S.-G. Chi, S. A. D'Souza, B. R. Nestok, R. W. devere White and The Cooperative Prostate Network, National Cancer Institute, 1996. Genes, Chrom. & Cancer,15:108–114.
11. CLONTech, Technical Services communication.
12. Abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp and Y, Tyr.
13. Fan, Y.-S., L. M. Davis and T. B. Shows, 1990. Proc. Natl. Acad. Sci. USA 87:6223–6227.
14. Bell, D. W., T. Taguchi, N. A. Jenkins, D. J. Gilbert, N. G. Copeland, C. B. Gilks, P. Zweidler-McKay, H. L. Grimes, P. N. Tsichlis and J. R. Testa, 1995. Cytogenet. Cell Genet. 70:263–267.
15. Sambrook J., Fritsch, E. F. & Maniatis, T. (1989) Molecular Cloning: A Laboratory Manual. 2nd Ed. Cold Spring Harbor Laboratory Press, Cold Spring Harbor, N.Y.
16. Golemis et al., (1996) Yeast Interaction Trap/Two Hybrid Systems to Identify Interacting Proteins, Unit 20.1.1–20.1.28 in *Current Protocols in Molecular Biology*, eds. Ausubel, F. M. et al., John Wiley & Sons, NY.

One skilled in the art will readily appreciate the present invention is well adapted to carry out the objects and obtain the ends and advantages mentioned, as well as those inherent therein. The nucleic acids, polypeptides, antibodies, recombinant animals, methods, procedures and techniques described herein are presented as representative of the preferred embodiments and intended to be exemplary and not intended as limitations in the scope of the present invention. Changes therein and other uses will occur to those of ordinary skill in the art which are encompassed within the spirit of the invention as defined by the scope of the appended claims.

What is claimed is:

1. An isolated CLAR1 nucleic acid molecule comprising a sequence selected from the group consisting of:
   a) SEQ ID NO: 1;
   b) a sequence encoding a polypeptide of SEQ ID NO: 2; and
   c) a sequence encoding a polypeptide of SEQ ID NO: 3.

2. The isolated CLAR1 nucleic acid molecule of claim 1, which is DNA.

3. The isolated CLAR1 nucleic acid molecule of claim 2, which is double-stranded DNA.

4. The isolated CLAR1 nucleic acid molecule of claim 2, which is a cDNA comprising a sequence approximately 2.6 kilobase pairs in length said cDNA encoding a late-stage-specific marker for prostate cancer progression.

5. The isolated CLAR1 nucleic acid molecule of claim 1, which is a cDNA comprising an exon, the exon of said cDNA specifically hybridizing with a nucleic acid of SEQ ID NO: 1, and said exon encoding a late-stage specific marker for prostate cancer progression.

6. A recombinant vector comprising a nucleic acid molecule according to claim 1.

7. A host cell comprising the vector according to claim 6.

8. An isolated RNA molecule transcribed from the double stranded nucleic acid of claim 3.

9. An isolated polypeptide, which is a product of expression of a nucleic acid molecule of claim 1.

10. An isolated human late-stage specific marker protein for prostate cancer progression encoded by the isolated CLAR1 nucleic acid molecule of claim 1, wherein the protein comprises a deduced molecular weight of between about 30 kDa and about 50 kDa, and wherein said protein comprises at least one SH3 binding domain and carboxy terminal serine phosphorylation site.

11. The protein of claim 10, comprising an amino acid sequence of Sequence I.D. NO: 2.

12. The protein of claim 10, comprising an amino acid sequence of Sequence I.D. NO: 3.

13. An antibody binding domain immunologically specific for part or all of the polypeptide of claim 9.

14. An antibody binding domain immunologically specific for part or all of the protein of claim 10.

15. The recombinant vector of claim 6, wherein said vector is selected from the group consisting of an *Escherichia coli* vector, a baculovirus vector and a *Saccharomyces cerevisiae* vector.

16. A method of diagnosing a susceptibility or predisposition to cancer in a patient indicated by the presence of CLAR1 comprising analyzing a patient sample using a method selected from the group consisting of a) a method of determining the presence, in a sample from a patient, of the CLAR1 nucleic acid molecule of claim 1;

b) a method of determining the presence, in a sample from a patient, of a polypeptide encoded by the CLAR1 nucleic acid molecule of claim 1 and, if present, determining whether the polypeptide is full length, and/or is mutated, and/or is expressed at a level associated with a susceptibility or predisposition to cancer;

c) a method of using DNA restriction mapping to compare a restriction pattern produced when a restriction enzyme cuts a sample of nucleic acid from the patient with a restriction pattern obtained from the CLAR1 nucleic acid molecule of claim 1;

d) a method of using a specific binding member capable of binding to the CLAR1 nucleic acid molecule of claim 1, the specific binding member comprising a nucleic acid hybridizable with the CLAR1 nucleic acid molecule, or a substance comprising an antibody domain with specificity for the CLAR1 nucleic acid molecule or a polypeptide encoded by it, the specific binding member being labelled so that binding of the specific binding member to its binding partner is detectable;

e) a method of using PCR involving one or more primers based on a nucleic acid sequence of the CLAR1 nucleic acid molecule of claim 1 to screen for a CLAR1 nucleic acid in a sample from a patient; and f) a method of using a specific binding member comprising at least one antibody domain with specificity for an epitope selected from the group consisting of a native CLAR1 nucleic acid epitope, and a polypeptide epitope encoded by the CLAR1 nucleic acid molecule of claim 1, the specific binding member being labelled so that binding of the specific binding member to its binding partner is detectable;

wherein said method further comprises the steps of determining whether the detected CLAR1 present in the patient is full length, and/or is mutated, and/or is expressed at a level associated with a susceptibility or predisposition to cancer; and determining whether the patient has a susceptibility or predisposition to cancer.

17. A method of identifying a CLAR1 nucleic acid molecule comprising a sequence selected from the group consisting of a) SEQ ID NO: 1; b) a sequence encoding a polypeptide of SEQ ID NO: 2; and c) a sequence encoding a polypeptide of SEQ ID NO: 3 in a test sample using a nucleic acid probe derived from the CLAR1 nucleic acid molecule and capable of specifically hybridizing to a complementary sequence of the CLAR1 nucleic acid molecule, the method comprising contacting the nucleic acid probe and the test sample under hybridizing conditions and observing whether hybridization takes place.

18. The method according to claim 17, wherein the nucleic acid probe is used to identify a mutant allele of the CLAR1 nucleic acid molecule.

19. A kit for detecting expression of a CLAR1 nucleic acid molecule comprising SEQ ID No: 1, the kit comprising at least one antibody capable of specifically binding a polypeptide encoded by the CLAR1 nucleic acid molecule.

* * * * *